US010941378B2

(12) United States Patent
Axelrod et al.

(10) Patent No.: US 10,941,378 B2
(45) Date of Patent: *Mar. 9, 2021

(54) METHOD FOR USE IN MONITORING BIOLOGICAL MATERIAL

(71) Applicant: VAYU SENSE AG, Munich (DE)

(72) Inventors: Noel Axelrod, Jerusalem (IL); David Nuttman, Ness Ziona (IL); Moria Shimoni, Petah-Tikva (IL)

(73) Assignee: VAYU Sense AG, Munich (DE)

( * ) Notice: Subject to any disclaimer, the term of this patent is extended or adjusted under 35 U.S.C. 154(b) by 800 days.

This patent is subject to a terminal disclaimer.

(21) Appl. No.: 15/614,994

(22) Filed: Jun. 6, 2017

(65) Prior Publication Data

US 2017/0267964 A1 Sep. 21, 2017

Related U.S. Application Data

(60) Division of application No. 14/571,489, filed on Dec. 16, 2014, now abandoned, which is a continuation-in-part of application No. PCT/IL2013/050520, filed on Jun. 17, 2013, which is a continuation-in-part of application No. 13/674,034, filed on Nov. 11, 2012, now Pat. No. 9,441,260.

(60) Provisional application No. 61/660,744, filed on Jun. 17, 2012.

(51) Int. Cl.
| | |
|---|---|
| *C12M 1/34* | (2006.01) |
| *C12Q 1/04* | (2006.01) |
| *G01N 21/39* | (2006.01) |
| *G01N 33/497* | (2006.01) |
| G01N 21/3504 | (2014.01) |
| G01N 33/02 | (2006.01) |
| G01N 33/49 | (2006.01) |

(52) U.S. Cl.
CPC ............ *C12M 41/34* (2013.01); *C12M 41/46* (2013.01); *C12Q 1/04* (2013.01); *G01N 21/39* (2013.01); *G01N 33/497* (2013.01); G01N 21/3504 (2013.01); G01N 33/02 (2013.01); G01N 33/49 (2013.01); G01N 2033/4977 (2013.01)

(58) Field of Classification Search
CPC ..... C12M 41/34; C12M 41/46; G01N 33/497; G01N 21/39; G01N 2033/4977; G01N 33/49; G01N 33/02; G01N 21/3504; C12Q 1/04

See application file for complete search history.

(56) References Cited

U.S. PATENT DOCUMENTS

| | | | |
|---|---|---|---|
| 4,889,992 A | 12/1989 | Hoberman | |
| 5,155,019 A * | 10/1992 | Sussman | C12M 41/34 250/343 |
| 5,482,842 A | 1/1996 | Berndt | |
| 6,486,474 B1 | 11/2002 | Owen et al. | |
| 6,955,652 B1 | 10/2005 | Baum | |
| 7,427,501 B2 | 9/2008 | Bachur | |
| 7,606,274 B2 | 10/2009 | Mirov et al. | |
| 7,738,104 B2 | 6/2010 | Kim et al. | |
| 8,994,948 B2 | 3/2015 | Tondello | |
| 9,441,260 B2 * | 9/2016 | Axelrod | C12Q 1/00 |
| 2008/0144677 A1 | 6/2008 | Belkin et al. | |
| 2011/0275112 A1 | 11/2011 | Sarver | |
| 2012/0113426 A1 | 5/2012 | Rao | |

FOREIGN PATENT DOCUMENTS

| | | |
|---|---|---|
| EP | 1724335 A1 | 11/2006 |
| EP | 2861984 B1 | 9/2019 |
| WO | 2006/047336 A2 | 5/2006 |
| WO | 2008/053507 A2 | 5/2008 |
| WO | 2010145892 A1 | 12/2010 |
| WO | 2012/001633 A2 | 1/2012 |

OTHER PUBLICATIONS

Tosi, S. et al., Assessment of In-Line Near-Infrared Spectroscopy for Continuous Monitoring of Fermentation Processes, 2003, Biotechnology Progress, 19, 1816-1821 (Year: 2003).*
Cristescu, S. M. et al., Laser-based systems for trace gas detection in life sciences, 2008, Applied Physics B, 92, 343-349 (Year: 2008).*
(Bugbee, B. et al., Absolute and Relative Gas Concentration: Understanding Oxygen in Air, 2006, Apogee Instruments, 1-9: http://www.apogeeinstruments.com/content/o2s_correcting.pdf (Year: 2006).*
Cussler, E. L. et al., Chapter 2—Diffusion in Dilute Solutions, 1997, Diffusion Mass Transfer in Fluid Systems, 13-49 (Year: 1997).*
Rogalski & Chrzanowski, "Infrared Devices and Techniques", Opto-Electronics Review 10(2), 111-136 (2002) (26 pages).
Arpi et al; A Novel Screening Method for the detection of microbial contamination of Platelet Concentrates, Vox Sang, 1993, 65:335-336.
Snyder et al; Extended Storage of Platelets in a New Plastic Container, Transfusions, 1985, vol. 25, No. 3.
CBS Report, Canadian Blood Services, 2010.
Weidmann et al., Carbon Isotopomers measurement using mid-IR tunable laser sources, Isotopes in Environmental and Health Studies, vol. 41, No. 4, Dec. 2005.
Weidmann et al., Development of a compact quantum cascade laser spectrometer for field measurements of CO2 Isotopes, Applied Physics, B 80, 225-260, 2005.

(Continued)

*Primary Examiner* — Louise W Humphrey
*Assistant Examiner* — Anjali Ajit Hirani
(74) *Attorney, Agent, or Firm* — M&B IP Analysts, LLC

(57) ABSTRACT

Presented herein is a method for in-situ real-time non-invasive estimation of the level of living cells proliferation and/or growth in a biological material present in a container sealed to prevent biological contamination. The method comprises measuring the concentration of at least one metabolic gas that is emitted by the living cells. The method can be adapted inter alia to detect a microorganism contamination in a storage container for platelets sealed to biological contamination, to monitor a fermentation process in a fermenter enclosing microorganisms and sealed to biological contamination, and to monitor the concentration of living cells in a bioreactor sealed to biological contamination.

12 Claims, 11 Drawing Sheets

(56) References Cited

OTHER PUBLICATIONS

S. Ribault et al., Journal of Clinical Microbiology vol. 2 (2004) pp. 1903-1908.
Mazarevica et al., Applied Spectroscopy, 58(7):804-810 (2004).
Threlkeld C.H., Journal of Food Science, 47:1222-1225 (1982).
Dhimitri K. et al., Canadian Light Source Activity Report, 190-191 (2009).
Tosi S. et al., Biotechnol. Prog., 19:1816-1821 (2003).
The International Search Report and the Written Opinion of the International Searching Authority for PCT/IL2013/050520, dated Sep. 18, 2013, ISA/EPO, Rijswijk, The Netherlands.

* cited by examiner

| Time [hours] | RPM | DO | pH | TEMP | OD |
|---|---|---|---|---|---|
| 0 | 50 | 93 | 7.00 | 37 | 1.07 |
| 1.0000 | 50 | 3.3 | 7.1 | 37 | 1.7 |
| 2.2333 | 317 | 6.0 | 7.1 | 37 | 3.6 |
| 3.3333 | 50 | 13.1 | 7.1 | 37 | 2.8 |
| 4.4500 | 50 | 14.2 | 7.11 | 37 | 3.5 |
| 5.4167 | 200 | 13.1 | 7.08 | 37 | 4.4 |
| 6.4167 | 300 | 5.1 | 7.1 | 37 | 6.28 |
| 7.6667 | 630 | 5.8 | 7.12 | 37 | 18 |
| 8.3333 | 800 | 3.8 | 7.19 | 37 | 28 |
| 9.3333 | 800 | 4.6 | 7.25 | 37 | 53 |
| 9.6667 | 800 | 28.4 | 7.31 | 37 | 53 |
| 10.1667 | 800 | 9.2 | 7.28 | 37 | 55 |
| 10.3333 | 620 | 22.6 | 7.29 | 30 | 55 |
| 22.1667 | 500 | 10.6 | 7.1 | 30 | 75 |
| 22.3333 | 471 | 9.8 | 7.1 | 30 | 76 |

METHOD FOR USE IN MONITORING BIOLOGICAL MATERIAL

TECHNOLOGICAL FIELD

The present invention in the field of monitoring the condition/status of a biological material, and relates to a method for detection of microorganisms and living cells in a biological material by optical measurements of metabolic gases.

BACKGROUND

Monitoring the live biological activity in a biological material is needed in various industries, for example in the medical field for monitoring microorganisms contaminants in blood/blood-components, in food and beverages (F&B) industries, and in pharmaceutical industries for example for monitoring fermentation processes.

Conventional techniques for monitoring biological activity in a biological material generally include direct techniques such as: viable count in which a diluted samples are grown on agar medium dish; staining or microscopy; pH and glucose measurements; swirling; and optical density (OD) measurements in which a sample of the biological material taken in to a cuvette and the level of microorganisms is determined optically based on turbidity of the sampled biological material itself. Other known techniques utilize monitoring the biological activity indirectly, for example based on analysis of gases consumption (such as dissolved oxygen—$dO_2$) or accumulated (such as carbon dioxide—$CO_2$) in a sample of the biological material. In those techniques, a sample of the biological material is incubated for a period of time to allow consumption or accumulation of gases by live microorganisms contained in the sample and then the metabolic gases are analyzed chemically and/or by utilizing spectroscopic measurements. However, conventional direct measurements made on samples of the biological material are invasive (thus increasing the risk of contamination of the biological material), time-consuming, and do not enable real-time monitoring of the growing population. Direct measurements of dissolved oxygen may be also inaccurate. For instance, in fermentation processes involving fungi, the diffusion of oxygen through the substrate does not occur at a uniform rate and therefore measurements with $dO_2$ electrodes when performed at lower oxygen diffusion rate may be misleading. Also, oxygen is a decreasing parameter that is limited by zero. On the other hand, conventional IR indirect techniques based on gas analysis in the container including the biological material are often influenced by the local conditions inside the container (e.g. temperature, pressure, humidity) and may lead to inaccurate measurements.

General Description

There is a need in the art for a novel technique for in-situ, real-time, noninvasive and accurate monitoring of biological materials, enabling the detection, monitoring and/or controlling of microorganisms and living cells in a biological material, such as blood components, food products and/or biological materials used in fermentation processes, for example those used in the pharmaceutical and/or food and beverages (F&B) industry. Specifically there is a need in the art for an in-situ real-time non-invasive accurate technique for detection of microorganisms in a culture media utilizing measurement of gaseous products generated during living cells growth/proliferation.

The known techniques for detecting metabolic gas concentrations in-situ are generally not sensitive and precise enough for correlate with bio growth of the microorganisms and living cells in biological material. The known techniques for detecting microorganisms' contaminations and/or grow in biological material by spectroscopic measurements of metabolic gas concentrations are generally not suited and/or are in-capable of in-situ real time operation. This is mainly because these techniques are invasive with respect to stored biological material that has to be inspected, i.e. they require sampling and incubation of the biological material in a separate sealed incubation container (sampling vial) which is impermeable for gases and possibly contains certain growth media. To this end, the conventional techniques utilize sampling/transferring certain amount of the biological material from a sealed container in which it is stored/maintained into a suitable sampling vial/container, which is specifically designed/selected to facilitate the spectroscopic measurements of metabolic gas(es). Conventional sampling vials used for this purpose are generally non-permeable to the metabolic gas in order to enable accumulation of high concentrations of the gas in the sampling vial. The conventional sampling vials are also specifically configured for the spectroscopic measurements (e.g. formed with specifically selected materials having high transitivity to wavelengths used in measurements). The sampled biological material is maintained in the sampling vial for sufficient time (the detection limit is only after incubation time of between 18 to 48 hours) for consumption or accumulation of relatively low or high concentrations, respectively, of gas consumed or accumulated by microorganisms contained in the biological material. As indicated above, many of the known techniques for growing biological material use incubation of a test sample while providing suitable growth conditions (e.g. providing growth medium such as agar, and/or incubating conditions/temperatures, and/or sufficient time for growth) to accelerate the microorganisms growth and accordingly accelerate production of the metabolic gases by the microorganisms contained in the sample. This is in fact because the sensitivity and/or accuracy of the known spectroscopic metabolic gas detection techniques require consumption or accumulation of relatively low or high concentrations, respectively, of the gas for the detection thereof.

The known techniques are thus not suited for in-situ real time non-invasive, accurate monitoring of biological activity/microorganisms in a biological material mainly because (1) they are invasive, i.e. require sampling of the biological material, (2) require specific equipment, i.e. the sampled biological material is transferred into a separate, specifically designed, sealed sampling vial (e.g. non-permeable to metabolic gases, highly transmitting for wavelengths used in spectroscopic measurements, e.g. containers made of glass/quartz), as well as typically require use of specific growth media, and (3) they are time consuming as they typically require relatively long incubation periods (e.g. 18-48 hours) of the sampled biological material for accumulation of sufficient (measurable/detectable) concentrations of the metabolic gases. Non-invasive gas monitoring methods available are not sensitive enough. In fact, in-situ, real time and non-invasive high resolution monitoring of biological activity in biological substances are needed in various fields. Specifically, such traits are needed in medical fields for handling blood and blood components for monitoring the blood/components thereof (e.g. prior to blood transfusions).

Also such traits are highly needed in various fermentation processes in which sensitive, real-time monitoring of the biological activity may provide substantial increase in the yield of the fermentation process. This would allow the control/monitoring of cells growth of a wide variety of microorganisms (including non-transparent and pathogenic ones), within various medium (including high turbidity/viscosity medium), early stage detection of cell growth, shorter R&D cycle time, and real time monitoring of biomass production process for increasing the yield (e.g. by determining optimal seed transfer and induction times, controlling the growth-media/biological-material composition utilizing controlled-depletion of nutrients, etc).

Specifically, one application of the invention is to detect bacterial contamination of a blood or blood-components, such as red blood cells, plasma and platelets, which are commonly used for transfusions. Particularly the invention provides for real time in situ non-invasive monitoring of microbiological contaminants in blood platelets which are a component of blood that is involved in blood clotting.

Allogenic blood/blood-components for transfusion are a potential source of infection by a variety of known and unknown transmissible agents. Over the last three decades, the risk of transfusion-related transmission of viral diseases such as human immunodeficiency virus (HIV) I/II, hepatitis C virus (HCV), hepatitis B virus (HBV) and human T-lymphotropic virus (HTLV) I/li has decreased dramatically. With blood products now being routinely screened by ultra-sensitive techniques to minimize the risk of transmitting viruses to recipients, the known risk of transmission of bacteria has emerged as the greatest residual threat of transfusion-transmitted disease.

Bacterial contamination has proved more difficult to address than viral contamination, and remains the most prevalent transfusion-associated infectious risk.

This is especially true for platelets, which are stored at room temperature (20-24° C.) for up to five days (rather than the previous practice of storage for up to seven days), in bags that are permeable to oxygen and carbon dioxide, and under sufficient constant agitation to provide adequate oxygenation, to prevent platelet aggregation and to maintain optimal platelet viability and functional properties.

Storage of the platelets at optimal metabolic conditions, at room temperatures, and with agitation in bags/containers permeable to $O_2$ and $CO_2$, promote ongoing bacterial proliferation throughout the storage period and thus increase the risk of transmitted bacteria and bacteremia in the patient. The risk of bacterial contamination in platelets is estimated to be one in 1500, which is 50 to 250 times higher than the combined risk of viral infections.

As described above, the conventional techniques for testing platelets for contaminants prior to transfusion are invasive (require opening of the sealed blood storage container for sampling thus increasing the risk of inadvertent contamination of the remaining platelets), require specific equipment and possibly growth media, and time consuming. Since the conventional techniques do not provide real time-pre transfusion reliable testing for contamination in platelet bag, the practical shelf life of platelets is decreased (from seven to five days) to avoid an increase in bacteria concentration to a levels that can cause sepsis in recipient.

In this connection, the present invention allows for in-situ non-invasive (without opening the container and withdrawing a portion of the biological material) real time and sensitive monitoring of a biological material, such as (but not limited to) a blood component, that can serve, intentionally or unintentionally, as a growth medium for the growth of microorganisms such as bacteria, and that is contained within a container sealed with respect to the biological material. The present invention provides for monitoring any biological material, such as food, human or animal tissues, and cell cultures, with particular application to blood components such as platelets. The technique of the present invention allows for detecting bacterial contamination in platelets contained/stored in conventional platelet storage bags (e.g. plastic bags) based on quantitative analysis of metabolic gases, such as $CO_2$, released by bacteria inside the platelet plastic storage bag which is permeable to metabolic gases, while the plastic storage bag with the platelets remains sealed to contaminates. Furthermore, as it will be explained in more details below, the detection of metabolic gas in the sealed container when performed according to the method of the present invention does not require a control/reference sample.

The concentration of the metabolic gas in a dead space associated with the storage bag is monitored by optical/spectroscopic measurements performed according to the technique of the present invention as described in more details below. The dead space, for the purposes of the invention, is a space/region which is free of the biological material under inspection and is in fluid communication therewith. In some embodiments, the dead space is defined by a region/portion of the container above a portion thereof containing the biological material. In some other embodiments, the dead space is defined by a gas chamber/reservoir/pipe connectable to the container (e.g. in a manner maintaining the sealing of the container), so as to be in the fluid communication with biological material in the container. Such reservoir/pipe may be formed by a separate cavity configured as an extension of the dead space in the container.

The measurements of metabolic gas concentration may for example utilize spectroscopic measurements in mid-IR spectrum of light at wavelength(s) overlapping with strong absorption line(s) of a metabolic gas (e.g. $CO_2$ or other metabolic gases). The light is transmitted through a part (dead space) of the plastic bag that is above the stored platelets, and is appropriately detected by an IR detector. The spectroscopic technique of the invention provides for determining the concentration of $CO_2$ or other metabolic gas by measuring light absorption within the plastic bag, while allows for discarding/discriminating the absorbance of the plastic bag itself, thus enabling in-situ monitoring of the metabolic gases contained in the dead space of the bag.

The technique of the invention allows the detection of different transfusion-relevant contaminating bacterial species. This approach provides on-line measurement of respiratory gases such as $CO_2$ at ambient atmospheric concentrations without the need for any pre-concentration or gas separation. The method is non-invasive since it does not require opening the plastic platelet bag for examination. This non-invasive bacterial detection method represents a new approach to prevent the transmission of bacterial contamination of platelets with an advantage of the method is that all measurements can be performed in real time, until right up to the time of transfusion and therefore the risk for sample errors is reduced to a minimum and the platelets' storage time is extended. Also, unlike conventional methods, the method of the present invention can be used with containers that are sealed with respect to the biological fluid, and are either impermeable or are permeable to the metabolic gas(es) being monitored. Some other possible applications of the invention include real-time, precise monitoring of fermentation processes. Owing to the specific features of the method and device of the invention, the monitoring is made possible for any kind of microorganisms (even pathogen) and any kind of culture medium (even those with high turbidity and/or viscosity). This allows the standardization of the monitoring procedure for any kind of fermentation process. In fermentation, the biological material generally added to the growth medium. Specifically for example, fermentation processes are used in the pharmaceutical industry for generating various biological substances such as: microbial cells (such as E. coli); microbial enzymes (catalase, amylase, protease, etc); primary metabolites (ethanol, citric acid, glutamic acid, etc); secondary metabolites (antibiotic, recombinant products: insulin, hepatitis B vaccine, interferon, etc).

The technique of the invention allows the detection of different microorganism's species including: aerobic & anaerobic; transparent & non-transparent; and pathogenic microorganisms. This approach provides on-line high resolution measurement of respiratory gases such as $CO_2$ at ambient atmospheric concentrations without the need for any incubation, gas separation, drying system or calibration. The detection method and system of the invention can apply qualitative and/or quantitative analysis and estimation of a level of biological activity of microorganisms, for example in agar plates, and monitoring of biological activity such as in the case of measuring living cells growth in the production of pharmaceutical products or proteins. Microorganisms are used commercially to produce foods (such as vinegar, yogurt, cause beer and wine spoilage), antibiotics and chemicals such as ethanol. Production of some of the most important and complex pharmaceuticals such as insulin, hormones, antibodies, or other proteins is carried out using microorganisms (such as E. coli) that have been modified genetically using recombinant DNA technology. From the early stages of commercial production of recombinant proteins and other pharmaceutical material, the handling of cultures has been subject to challenges. One of these challenges is how to cope with the problem of instability of production processes as in the case of recombinant organisms and induction. Commercial production of products on a large scale, especially in the pharmaceutical industry using fermenters, depends heavily on the stable maintenance of the organisms during production and harvesting time. The fermentation process of recombinant bacteria needs to be precise and the cells concentration has to be monitored.

For clarity, in the following description, monitoring of pharmaceutical fermentation processes for generating proteins is specifically described. However it should be understood that the present invention can be used for real time monitoring of other fermentation processes in the pharmaceutical industry and/or in the F&B industries.

In fermentation, specific microorganism species are deliberately introduced into a fermentation container containing a biological material serving as growth medium. The fermentation container is kept at suitable conditions (e.g. glucose, yeast, agitation, temperature) encouraging the production of the desired biological substances/proteins by microorganism. Typically, a gas inlet is coupled to a fermentation container to supply suitable atmospheric conditions for the microorganisms' metabolism (e.g. supply of ambient air) and a gas outlet is also coupled to the fermentation container to evacuate gas which is richer in metabolic gases generated by the microorganisms' metabolism. In many cases, fermentation processes are monitored by occasionally collecting a sample from the biological material in the container and analyzing that sample (such as OD measurements) in order to determine data indicative of the amounts of microorganisms and/or the amount of the produce material or proteins in the sample, and utilize that data for controlling the fermentation process.

The amount of the biological substance, which is to be produced in the fermentation, is generally correlated with the amount/the rate of change of the amount of microorganisms in the biological material in the container. To this end, an accurate real-time monitoring of the amount of microorganisms enables accurate control over the fermentation process and provides for significantly increasing the yield of the product to be produced.

For example, the production of recombinant protein is correlated with an optimal induction process and microorganisms' amount. During the first stage, log (logarithmic) phase, the microorganisms is being grown to certain, very specific, well define amount in which an inducer added to the culture media. Then at a later/second stage, the recombinant bacteria stops proliferating and use their "cell energy" for the production of the recombinant protein. Problems that may occur during bacteria log phase (due to problems with nutrients, for example), lack of precision during induction and/or over grown of the bacteria may lead to lower yield. Thus, by monitoring a time profile of the amount of microorganisms and/or changes thereof, the fermentation process can be controlled to improve the yield of the generated product and harvesting time (see FIG. 9).

However, the conventional techniques for monitoring biomass in fermentation processes are not performed continuously and are incapable of being carried out with high sensitivity in real time, and typically involve occasional collection of samples from the fermentation container and examining these samples by techniques such as optical/ critical density measurement, viable counts, and by measuring the produced material. These results, inter alia, in that the optimal time points for collection of fermentation yield are often missed.

The present invention provides for an accurate real time and continuous/periodical monitoring of fermentation process by continuous/periodical monitoring of the atmospheric conditions in the container to determine data indicative of a rate of metabolic gas production by microorganisms contained therein, or a change in such rate of production, and thereby determining the amount of the microorganisms, biomass, or the rate of change in this amount. The later are processed to control the fermentation process accurately in time such as to improve the yield. For example the monitored amount of microorganisms and/or rate of change thereof may be compared with a reference data/model to control the fermentation conditions (e.g. temperatures of the fermenter, gaseous atmosphere therein, nutrients or other materials supplied during the fermentation process etc), and/or identify a time at which the fermentation process transit from the "first" (production stage) to the "second" ("proliferation stage") stages, for stopping, harvesting or managing the process at this time.

The system of the present invention may be configured to continuously and/or periodically/repeatedly monitor the gas/ atmosphere in the fermentation container and may be in optical communication with the gas within the container itself (e.g. above the biological material) and/or in optical communication with a gas flowing out from the fermentation container (e.g. gas being in fluid communication with the inside of the container, for example gas flowing through the gas outlet of the container).

Yet another attractive application of the present invention is related to detection of isotopologues of metabolic gases. Isotopologues are molecules that are identical except for their isotopic composition. Examples of the isotopologues of carbon dioxide are $^{12}C^{16}O_2$, $^{13}C^{16}O_2$, $^{16}O^{12}C^{18}O$, $^{16}O^{13}C^{18}O$. The natural abundance of isotopologues that contain a rare isotope is negligible in comparison to the common molecule. For example, the natural abundance of $^{13}C^{16}O_2$ is 0.0111%, and the natural abundance of $^{18}O^{13}C^{18}O$ is 10-8. Different isotopologues of the same molecules have different vibration frequencies, and thus different absorption spectra in the IR region. For example, molecules of $^{13}C^{16}O_2$ have a strong absorption at 2270.29 cm$^{-1}$, while the absorption strength of the nearest absorption line of $^{12}C^{16}O_2$ at 2277.427 cm$^{-1}$ is weaker by a factor of about 30 than that of $^{13}C^{16}O_2$. This provides means for discrimination between different isotopologues of the same molecules by means of infrared absorption spectroscopy. In particular, a typical tunable QCL operating in continuous wavelength (CW) mode can have a beam spectral width as narrow as 0.01 cm$^{-1}$. That provides means for unambiguous measurement of concentrations of isotopologues of a molecule under study in a setup as described above. Isotopologues can serve as biomarkers to trace particular metabolic processes. One example of such an application is the use of D-glucose-$^{13}C_6$ as a carbon based nutrition source for bacteria for checking specific metabolic processes, that in turn can be used for example to study the efficiency of the fermentation reaction of glucose for ethyl alcohol production at different stages of the fermentation process.

Thus, the present invention provides a novel method for in-situ nondestructive (non-invasive) real time detection of microorganisms in biological materials.

It should be understood that the term biological material herein relates to any material that can serve as culture media for growth of microorganisms and/or living cells. In this regards, this term includes and is not limited to blood and blood components such as platelets, F&B products and biological materials used in fermentation processes (e.g. in the F&B and/or pharmaceutical industries). Also the term microorganisms relates to any living organisms such as bacteria, fungi etc. The term metabolic gas relates to one or more gases produced or consumed by microorganism's metabolism, and may include for example gases such as carbon dioxide (CO$_2$) produced during respiration. Some not limiting examples of gases that are specifically included in this definition are carbon dioxide, oxygen, ammonia, hydrogen sulfide, methane, ethane, butane, ethylene, sulfur dioxide, carbonyl sulfide and nitric oxide. Examples of gases that are specifically excluded from this definition include argon and inert gases such as helium or nitrogen which do not participate in the metabolic process. For clarity, in the following description, the present invention is described specifically in relation to the carbon dioxide metabolic gas. Nevertheless it should be understood that the technique of the present invention is not limited to carbon dioxide and can also be applied to detection microorganisms based on other metabolic gases.

It should further be noted that the term in situ in the context of the current disclosure refers to detection of microorganisms being performed directly on metabolic gas(es) formed in the original storage/fermentation container (at times termed herein as biological material (BM) container), without sampling or opening the BM container. To this end, the detection is performed without a need to expose the biological material in the container to external microorganisms. In this regards, the term in-situ measurement should be interpreted broadly, as including analysis of the gas(es) directly inside the storage container/bag of the biological material, where the term directly signifies applied to gas(es) in a dead space being in fluid communication with the biological fluid in the storage container, namely a portion of the container itself or a reservoir/pipe non-invasively connectable to the portion of the container. For example, metabolic gas detection may be performed at the gas outlet of a fermentation container and/or at a certain gas reservoir connectable to a BM container of blood/blood-components (e.g. bag/vial) by a fluid connection that does not permit external microorganism contaminant into the BM container (e.g. utilizing a transfusion needle to connect the gas-chamber/reservoir to the BM container to allow gas flow to the reservoir without opening the BM container.

In this regards, the detection is non-invasive and nondestructive in the sense that measurement procedure does not destroy or affect in any way the biological material, and thus the biological material can still be used for its original purpose, after the detection procedure. The detection is real-time in the sense that no incubation period is required and the results of the detection can be obtained within a relatively short time scale (seconds or minutes).

The goal of the detection is to determinate the presence of microorganisms such as bacteria (e.g. bacteria contamination) in the biological material. Yet it can be quantitative analysis and estimation of level of biological activity of microorganisms for example in agar plates and also monitoring of biological activity of microorganisms such as in case of fermentation process.

Thus, according to one broad aspect of the invention, there is provided a method for use in detection of microorganisms in a biological material, the method comprising:

(i) applying non-invasive in-situ optical measurements to a region of interest being a dead space free of a biological material and in a fluid communication with a portion of a container containing the biological material, wherein the optical measurements comprise illuminating the region of interest with light including at least first and second predetermined wavelengths of substantially narrow spectrum corresponding to respectively an absorption peak of at least one metabolic gas and a spectral region outside the absorption peak of the at least one metabolic gas, and measuring transmission of the first and second wavelengths through the dead space; and (ii) analyzing measured data of the transmission and generating data indicative of a concentration of the at least one metabolic gas in the dead space which is in the fluid communication with the biological material, the generated data being thereby indicative of microorganisms in the biological material.

The measurements of metabolic gas concentration may generally be performed utilizing infrared and/or visible portions of electromagnetic radiation.

According to some embodiments of the present invention the method further includes processing the data indicative of the concentration of the at least one metabolic gas utilizing equilibrium condition between a rate of generation or consumption of the at least one metabolic gas by the microorganisms and a rate of flow of the at least one metabolic gas into and/or out of the container. Then utilizing the equilibrium condition data about the microorganisms in the biological material is obtained/determined.

According to some embodiments of the present invention the spectral width of the substantially narrow spectrum of the first wavelength overlaps and exceeds a spectral width of an absorption line of the metabolic gas. Also, in some cases, the spectral width of the first wavelength is less than a spectral distance between two spectrally adjacent absorption lines of the metabolic gas.

Moreover in some cases the spectral separation between the first and second wavelengths of the light source is substantially small such that the first and second wavelengths are characterized by same or similar transmission through predetermined materials used for containers of the biological material. In this connection, according to some embodiments the transmission of the second predetermined wavelength (being in the spectral region outside the absorption peak of the metabolic gas), is indicative of absorbance of the first wavelength by materials in the region of interest, other than the metabolic gas. These other materials typically have a spectral absorbance band substantially wider than that of the absorption peak of the metabolic gas. Thus analyzing the measured data of the transmission may include utilizing the measured transmission of the second predetermined wavelength to process the measured data of the transmission of the first predetermined wavelength, which overlaps the absorption peak. This increases the sensitivity in determination of the concentration of the metabolic gas and allows detection of the microorganisms.

The high sensitivity of detection enables determination of the concentration of the metabolic gas based on equilibrium condition between a rate of generation or consumption of the at least one metabolic gas by the microorganisms and a rate of flow of the at least one metabolic gas into and/or out of the container. Also, in cases where the region of interest at which measurements are conducted is the dead space above the portion with the biological material in the container, the high sensitivity and the use of the above mentions first and second types of wavelengths may provide for eliminating a need for a-priory knowledge of optical properties of the container.

The at least one metabolic gas may include one or more of the following: carbon dioxide, oxygen, ammonia, hydrogen sulfide, methane, ethane, butane, ethylene, sulfur dioxide, carbonyl sulfide and nitric oxide. In some embodiments the metabolic gas includes carbon dioxide and the at least first and second wavelengths are in a spectral regime of high absorbance by carbon dioxide. Specifically the first wavelength overlaps one of absorption peaks of carbon dioxide in that regime, and the second wavelength overlaps a transmission peak in the carbon dioxide spectrum. For example the spectral regime may be in a mid-IR regime (e.g. spectral regime of high absorbance by $CO_2$ is in the vicinity of 4.3 microns). According to some embodiments of the present invention the optical measurements include spectroscopic measurements. According to some embodiments of the present invention, the illuminating the dead space (the region of interest to be measured) includes operating a broadly tunable coherent IR light source, for producing light of the above mentioned at least first and second wavelengths. The light is directed to propagate along a path of a certain predetermined optical path (length) through the dead space and, the method includes operating a detection module for detecting the light transmitted through the dead space. In some cases, the broadly tunable coherent IR light source is a Quantum Cascade Laser (QCL). Also in some cases, operating of the broadly tunable coherent IR light source includes modulating light intensity in the at least first and second wavelengths, and operating a lock-in amplifier (associated with the detection module) to determine the transmission of the region of interest to the modulated first and second wavelengths with high signal to noise ratio signal detection based on the modulation.

According to some embodiments the optical measurements are applied to the dead space of the container, while the container is remained sealed with respect to the biological material under measurements. To this end, in some cases the container may be permeable to the at least one metabolic gas and data about the microorganisms in the biological material are determined based on an equilibrium condition defined by diffusion of the at least one metabolic gas through walls of the container. To this end the container may be a storage container for platelets, such as a conventional platelets storage container.

According to some embodiments the optical measurements are applied to the dead space of the container, where the dead space may be defined by one or more of the following: (i) a portion of the container above the portion containing the biological material; (ii) a gas chamber configured to be connectable to the container so as to be in the fluid communication with the closed container (e.g. the gas chamber may be a gas outlet of the container; (Ili) an extension of the dead space of the container by an attached reservoir transparent to the at least first and second wavelengths.

In some embodiments of the present invention the container is configured for use in a process of fermentation. The optical measurements may be performed through one or more optical windows optically coupled to the dead space of the container. In some cases, for monitoring the fermentation process, the optical measurements and the data analysis are performed continuously or periodically. Accordingly the determined gas concentration data being thereby indicative of at least one of: (a) amount of microorganisms in the container as a function of time; and (b) a rate of change in amount of microorganisms in the container as a function of time. Thus method further includes processing the gas concentration data to monitor the fermentation process.

According to some embodiments the method of the present invention for determining the concentration of at least one metabolic gas, includes:

(i) measuring IR transmission through the dead space in two or more wavelengths comprising the above noted first and second wavelengths. The measuring comprises: tuning a central wavelength of illuminating light each one of the two or more wavelengths; detecting IR light in the two or more wavelengths transmitted through the dead space; and generating measured data indicative of two or more intensity values comprising first and second intensity values corresponding to the light transmitted through the dead space in the first and second wavelengths for a given optical path defined by the optical system and the dead space; and (ii) processing the measured data based on an absorption model of the at least one metabolic gas. The processing comprises determining a best fit between intensity values obtained from the absorption model and the measured intensity values, and thereby determining the concentration of the at least one metabolic gas.

In some embodiments the method further includes utilizing the concentration of the metabolic gas for estimating a degree of microbial contamination of the biological material.

In another broad aspect there is provided a system for use in carrying out the method of the invention for detection of microorganisms in a biological material. The system includes:

(a) an optical system including: a broadly tunable coherent IR light source and a detection module that includes a detector sensitive in the IR wavelength regime. The broadly tunable coherent IR light source is configured and operable for producing light in a predetermined spectrum including at least first and second predetermined wavelengths of substantially narrow spectra corresponding to respectively an absorption peak of at least one metabolic gas and a spectral region outside the absorption peak of the at least one metabolic gas. The detection module is configured for detecting light of the first and second wavelengths passing through a region of interest (e.g. being a region located in between the light source and the detection module). The detection module is configured for generating data indicative of transmission of that region of interest to the at least first and second wavelengths; and (b) a control system connectable to the light source and to the detection module and configured and operable for carrying out the following:

operating the light source to produce the light of at least the first and second wavelengths. The first wavelength is selected such that the detected transmission for the first wavelength provides measured data indicative of absorbance by the at least one metabolic gas in the region of interest. The second wavelength is selected such that the detected transmission for the second wavelength provides detection of measured reference data indicative of absorbance of the first wavelength by materials in the region of interest other than the at least one metabolic gas;

receiving and analyzing the measured data and the measured reference data, and generating data indicative of the concentration of the metabolic gas in the region of interest. This thereby enables non-invasive in-situ detection of microorganisms in a biological material when located in fluid communication with the region of interest. According to some embodiments of the present invention the light source is broadly tunable light source having a tunability range of at least 2 cm$^{-1}$. The broadly tunable light source may be a Quantum Cascade Laser (QCL) with a tunability range exceeding 30 cm$^{-1}$. In some embodiments, the detection module includes a lock-in amplifier, and the control system is adapted for operating the broadly tunable IR light source for modulating light intensity of the at least first and second wavelengths, and operating the lock-in amplifier to determine the transmission of the region of interest to the at least first and second wavelengths with high signal to noise ratio based on the modulation. To this end the optical system is configured to define illumination and detection paths for the light of the at least first and second wavelengths intersecting with the region of interest for placement, in the region of interest, a dead space, which is free of the biological material and is in fluid communication with a portion of a container containing the biological material. In this connection in some embodiments the system of the present invention may further include a mechanism for positioning the container of the biological material with respect to the optical system, such that the illumination and detection paths intersect with the dead space of the container and traverses a predetermined optical path (length) through the dead space. It should be understood that in various embodiments of the present invention, the system of the invention and/or its controller (control system) may be configured and operable for carrying out various operations of the method described above and more also described more specifically below.

According to another broad aspect of the present invention there is provided a method for use in detection of microorganisms in a biological material. The method includes:

(i) applying non-invasive in-situ optical measurements to a region of interest being a dead space free of a biological material and in a fluid communication with a portion of a container containing the biological material. The optical measurements include illuminating the region of interest with light of a predetermined substantially narrow spectrum including two or more predetermined wavelengths and measuring transmission of the two or more wavelengths through the dead space;

(ii) analyzing measured data of the transmission and generating data indicative of a concentration of the at least one metabolic gas in the dead space which is in fluid communication with the biological material; and (iii) processing the gas concentration data based on an equilibrium condition between a rate of generation or consumption of the at least one metabolic gas by the microorganisms and a rate of flow of the at least one metabolic gas into and out of the container, thereby generating data indicative of microorganisms in the biological material.

According to another broad aspect of the present invention there is provided a container including: a sealable main body for containing a biological materials and being permeable to at least one metabolic gas; and a reservoir being configured for fluid communication with the sealed main body, and having at least a portion thereof at least partially transparent to one or more wavelengths corresponding to at least one absorption peak of the at least one metabolic gas.

According to yet another broad aspect there is provided a reservoir for use in inspection of biological material contained in a sealed platelets storage container permeable to at least one metabolic gas. The reservoir is connectable to the container, so as to be in fluid communication with a dead space in the container (above a portion thereof where the biological material is contained) while the container is maintained sealed with respect to the biological material and contaminates/microorganisms. Also the reservoir has at least a portion thereof which is at least partially transparent to one or more wavelengths corresponding to at least one absorption peak of at least one metabolic gas.

The present invention thus provides novel, effective and simple technique for accurate in-situ real time non-invasive monitoring of a biological material for detection microorganisms therein. Additional features and elements of the present invention are described in more details in the detailed description of embodiments below.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The principles and operation of in-situ real-time and non-invasive detection of microorganisms in biological materials according to the present invention may be better understood with reference to the drawings and the accompanying description.

The inventive technique is based on measuring the absorption of illuminating light (typically in the infrared spectrum) transmitted through a gaseous atmosphere in fluid communication with the biological material, e.g. in a portion of a storage container above the biological material. Living microorganisms produce metabolic gases such as carbon dioxide ($CO_2$) during respiration. By means of infrared absorption, the concentration of metabolic gases can be measured inside the storage container.

Figure 1A:
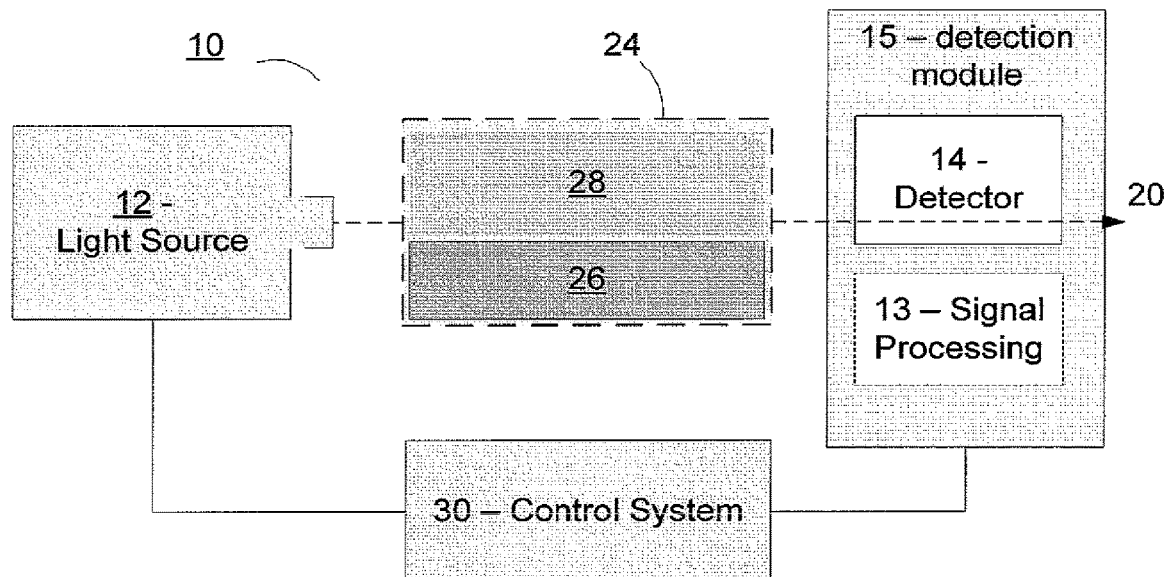
FIG. 1A is a block diagram schematically illustration a system for detecting microorganisms in biological material.

Reference is made to FIG. 1A illustrating schematically in a block diagram a system 10 for detection of microorganisms in a biological material. The system 10 includes an optical system which includes a tunable broadband IR light source 12 and a detection module 15. The tunable broadband IR light source 12 is configured and operable for emitting light in a predetermined substantially narrow spectrum. The tunable broadband IR light source 12 is controllably operated for emitting light in at least a first and a second predetermined wavelengths, wherein the first wavelength corresponds to an absorption peak of at least one metabolic gas to be detected, and the second predetermined wavelength is in a spectral region outside the absorption peak of the at least one metabolic gas. The detection module 15 includes a detector 14 sensitive in the IR wavelength regime. The light source and the detection module are arranged to form respectively illumination and detection paths, e.g. being in optical communication with one another, intersecting a region of interest. The detection module is configured and operable for detecting light in the first and second wavelengths, such as light passing through the region of interest located in between the light source 12 and the detector 14, and generating intensity data/signals indicative of the intensity of detected light in the first and second wavelengths. This data is therefore indicative of the transmittance of the region of interest to the at least first and second wavelengths.

Further provided in the system 10 is a control system 30 (e.g. controller), which is connectable to the optical system, i.e. to the light source 12 and to the detection module 15. The controller 30 is configured and operable for operating the light source 12 to emit light in the selected at least first and second wavelengths, and for receiving and analyzing measured/detected data/signals from the detection module and generating data indicative of a concentration of the metabolic gas in the region of interest.

In some embodiments, the light source 12 and the detector 14 are arranged in space-apart relationship defining the region of interest there between for spectroscopic measurements. To this end, light source 12 and the detector 14 are arranged such that a suitable container 24 of a biological material 26 and/or more specifically a dead space 28 associated with and being in fluid communication with such container 24 can be placed. The biological material is that in which microorganisms should be detected by optical/spectroscopic measurements performed by the system 10 of the present invention. As indicated above, the dead space 28 of the container is actually any space being in fluid communication with the atmosphere in the container above biological material 26. This may include any one of the following: the portion 28 of the container 24 above the biological material as illustrated for example in FIG. 1A, and/or any suitable gas-chamber such as a reservoir and/or an outlet pipe/tube connected to the container and being in fluid communication with its atmosphere, as will be described below with reference to FIGS. 2A-2B and 5B.

The analysis of the measured data is generally based on the principles of spectroscopy. However, in the present invention, the first and second wavelengths are particularly selected to enable accurate and high-sensitivity measurements of the concentrations of one or more metabolic gases, even in noisy environment, possibly having a wide range of unknown parameters. The first wavelengths is selected to be highly affected by absorbance by the at least one metabolic gas in the region of interest, i.e. to overlap with the absorption line (at times termed herein as "peak"). The second wavelength is on the other hand selected to be less affected by absorbance of the metabolic gas, but nevertheless it is selected to be spectrally close to the first wavelength, such that it provides reference data indicative of absorbance of the first wavelength by other materials in the region of interest. For example the distance between the first and second wavelengths may in some embodiments be about half of distance between two absorption lines of the metabolic gas, or in some embodiments the second wavelength may be located outside the spectral range including intense absorption lines of the metabolic gas. This is exemplified in and described in more details below with reference to FIGS. 1C and 10.

In this regards, it should be noted that the inventors have found that some metabolic gases are associated with spectral regimes of high absorbance in which sharp absorbance peaks exist in the vicinity of sharp transmission peaks (absorbance valleys). On the contrary, the absorption spectra of various materials (e.g. polymer, plastic of which various containers are made as well as vapors such as water vapors), which are in many cases located in the optical path of the measured gaseous media and impede accurate spectroscopic measurements of such metabolic gases, are typically associated with relatively broad and non-volatile spectral profile which does not have sharp peaks. Taking advantage of this finding, some embodiments of the invention utilize the so-selected second wavelength to provide reference to the absorbance of the first wavelength by materials other than the metabolic gas in the vicinity of the region of interest. This can be done because the spectral distance between the first and second wavelengths is selected such, or is sufficiently small, such that the first and second wavelengths exhibit same or nearly similar absorption by various materials possibly located in the optical path.

Thus, the at least two wavelengths are specifically selected such that the one of them is highly absorptive by the metabolic gas to be detected (which concentration is to be measured) and the second is selected to be less absorbed by the metabolic gas but absorbed to similar level (as the first wavelength) by other materials conventionally/typically located in the optical path of measurements. This allows for in situ non-invasive optical/spectroscopic measurements of the metabolic gas concentration with high accuracy and/or high sensitivity while not reducing the effects of unknown materials/condition in the vicinity and/or in the region of interest of the measurement.

In this connection it should be understood that in some embodiments the method of the present invention is adapted for conducting optical measurements in more than two wavelengths; e.g. with one or more wavelengths of the first type—highly absorbed by the metabolic gas, and/or with one or more wavelengths of the second type—less/negligibly absorbed by the metabolic gas. More specifically a coherent broadly tunable light source (e.g. Mid-IR light source) is used to emit light at first type wavelength overlapping with absorption line(s) of the metabolic gas and having a spectral width wider than that of the absorption line. In the description below the term overlapping is used also to denote that the spectral width of the light source exceeds the spectral width of metabolic gas ($CO_2$) lines. This ensures robustness and high repeatability of the measurements. More precisely, the spectral width of the light source is preferably more than the spectral width of the absorption line, but less than the distance between two adjacent spectral absorption lines. Thus, during a wavelength scan of the laser/light-source, the scanning accuracy with spectral resolution comparable or higher than the spectral width of the light source in order to enable to tune the light source to overlap/cover the absorption line. The use of light source with spectral width exceeding the spectral width of absorption lines provides that spectral resolution of tuning needs not to be higher than the width of the gas absorption line, which may be very small (e.g. wave-number below 0.05 $cm^{-1}$) and which spectral resolution of tuning is hard to achieve. Also, the spectral width of the absorption line is a function of gas pressure and temperature. Hence utilizing a light source having spectral width exceeding the width of absorption line decreases the sensitivity of the variations of the spectral width of the absorption lines thus improving the robustness of the measurements under varying conditions (temperatures and pressures). Also the condition that the spectral width of the light source is less than the distance between two adjacent spectral absorption lines ensures high contrast and/or resolution when measuring at the second type wavelength, away from the maximum absorption.

In fact, in some embodiments the light source 12 is a broad-band tunable light source with sufficiently narrow spectral peak. The control system 30 is in communication (by wires or wireless signal communication) with the light source 12 and configured for swiping the wavelength emitted by the light source 12 (continuously or discretely) over a certain wavelength range including several absorption peaks and/or valleys of absorption in the absorption spectra of the metabolic gas to be detected. The control system is also in communication (by wires or wireless signal communication) with the detection module (e.g. for operating it) for receiving measured data indicative of transmission of the several wavelengths in this spectral ranges such that one or more of the wavelengths correspond to the first type wavelength and one or more of them correspond to the second type wavelength. This procedure, in which data on transmission of more than two such wavelengths is acquired, is used in some cases, to further improve the accuracy and sensitivity of the system and method of the present invention event in very noisy scenarios.

It should be understood, although not specifically illustrated, that the control system is typically a computer system including inter alia digital or analog input and output ports, memory, data processor, and may be implemented as hardware and/or software modules. Such a computer system may be at least partially integral with the detection module.

In some embodiments of the present invention, the light source 12 is configured for emitting substantially monochromatic light, which narrow spectral width is in the order of the width of certain spectral peaks/features in the absorbance profile of the metabolic gas to be detected. For example, in some cases the light source 12 is a tunable IR light source/laser. In particular the light source may be selected to be tunable within a certain wavelength band in the mid-IR regime (the term mid-IR is used herein to designate wavelengths of light in the spectral range of 3 to 30 microns. In some particular embodiments of the system 10 of the present invention the tunable quantum cascade laser (QCL) is used as the light source 12, since it provides wide wavelength tunability and sufficiently narrow spectral width (sufficiently monochromatic light emission). Alternatively or additionally, the light source 12 can also be a broadband source equipped with suitable narrow-band spectral filters in the mid-IR regime. The use of a tunable light source instead of the fixed wavelength source allows for determining the metabolic gas concentration within the container without using any etalon.

The detection module 15 may include an IR detector 14 whose output is connected to an electronic signal processor/amplifier 13. In some embodiments, the electronic signal processor 13 includes or is constituted by a lock-in amplifier.

In some cases, the at least one first wavelength is selected to be in a spectral regime of high absorbance of carbon dioxide (being the probed metabolic gas) such that first wavelength overlaps an absorption peak/line of carbon dioxide in this regime. For example the at least one first wavelength may be in the wavelength band in the vicinity of 4.3 microns which corresponds to spectral regime of high absorbance by $CO_2$. Indeed, in some cases also the second wavelength is selected close to the first wavelength and in the similar regime of high absorbance by the metabolic gas. However the second wavelength is specifically selected/tuned to fall outside of an absorption line (e.g. in an absorption valley) of the carbon-dioxide/metabolic gas such that it only provides a reference to the absorbance by other material in this regime.

Figure 1B:
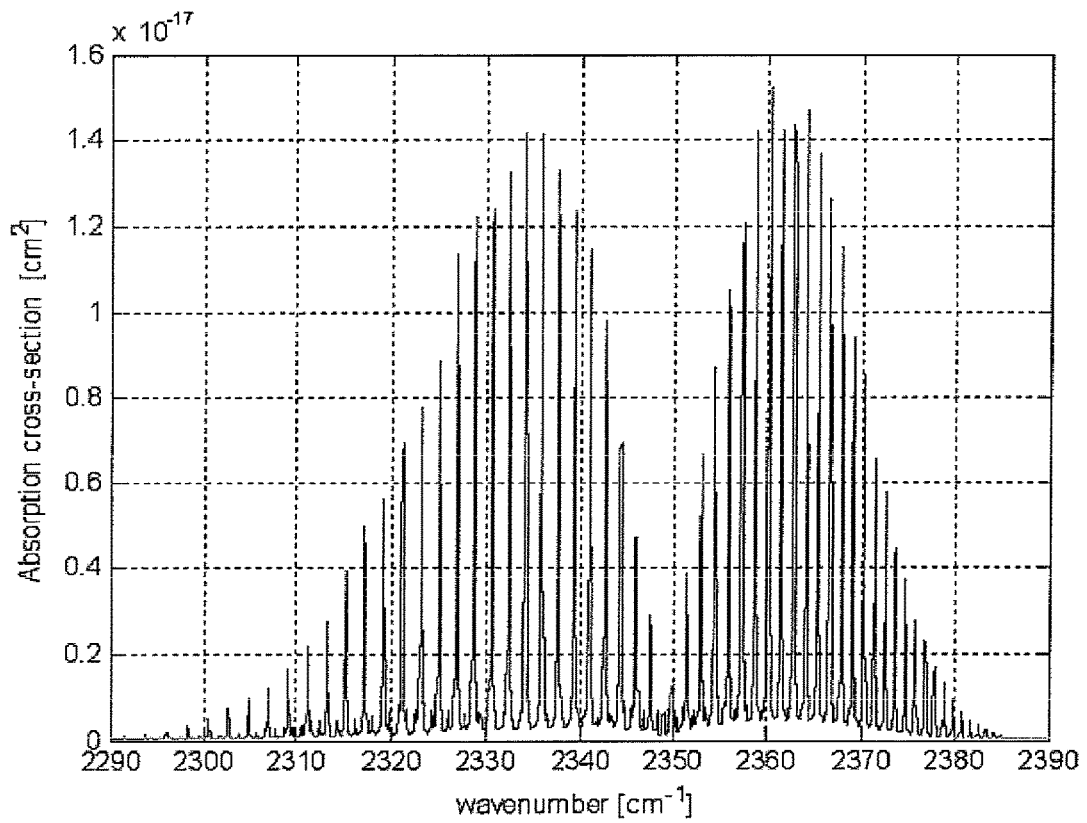
FIG. 1B is a graph exemplifying absorption cross section of metabolic carbon dioxide ($CO_2$) gas at ambient conditions.
Figure 1C:
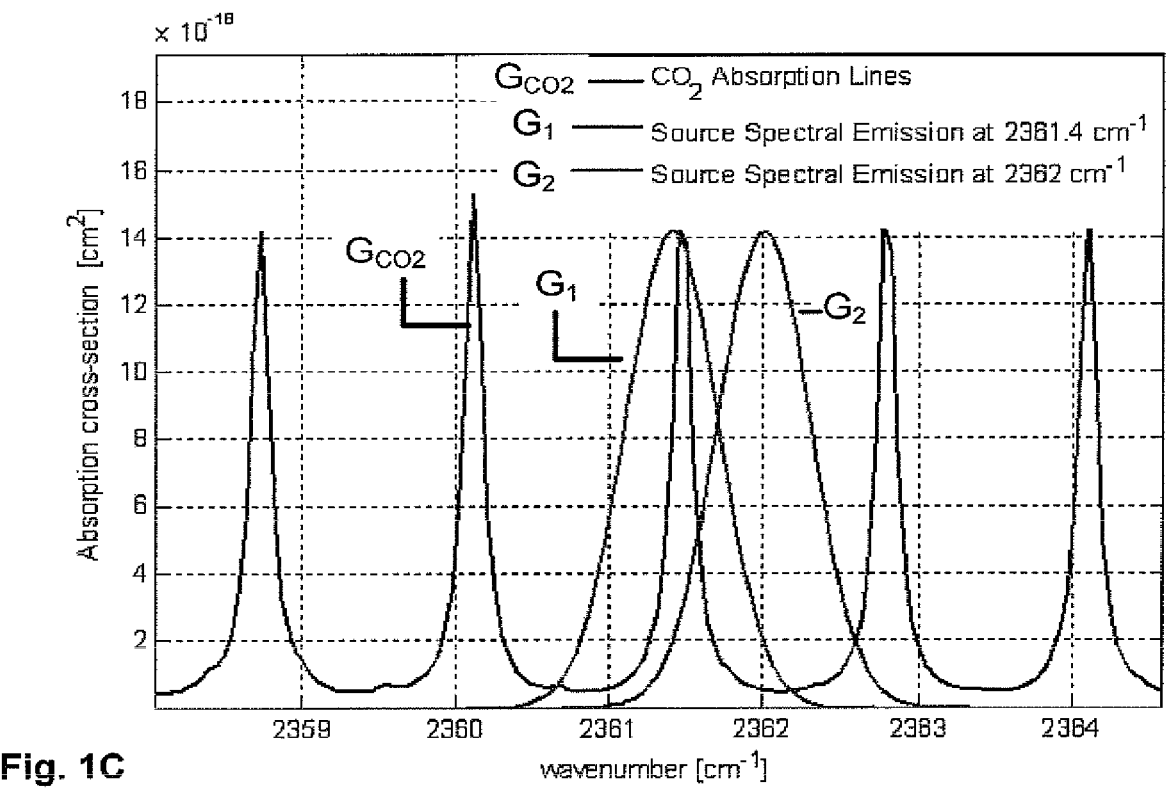
FIGS. 1C and 1D respectively illustrate two examples of the spectrum of light beams of first and second wavelengths suitable for use in the invention, where the first and second wavelengths are respectively superposed to overlap/cover an absorption peak (absorption line) and absorption valley (transmission line) of the $CO_2$ absorption spectrum in the mid-IR wavelengths band near 4.3 microns.
Figure 1D:
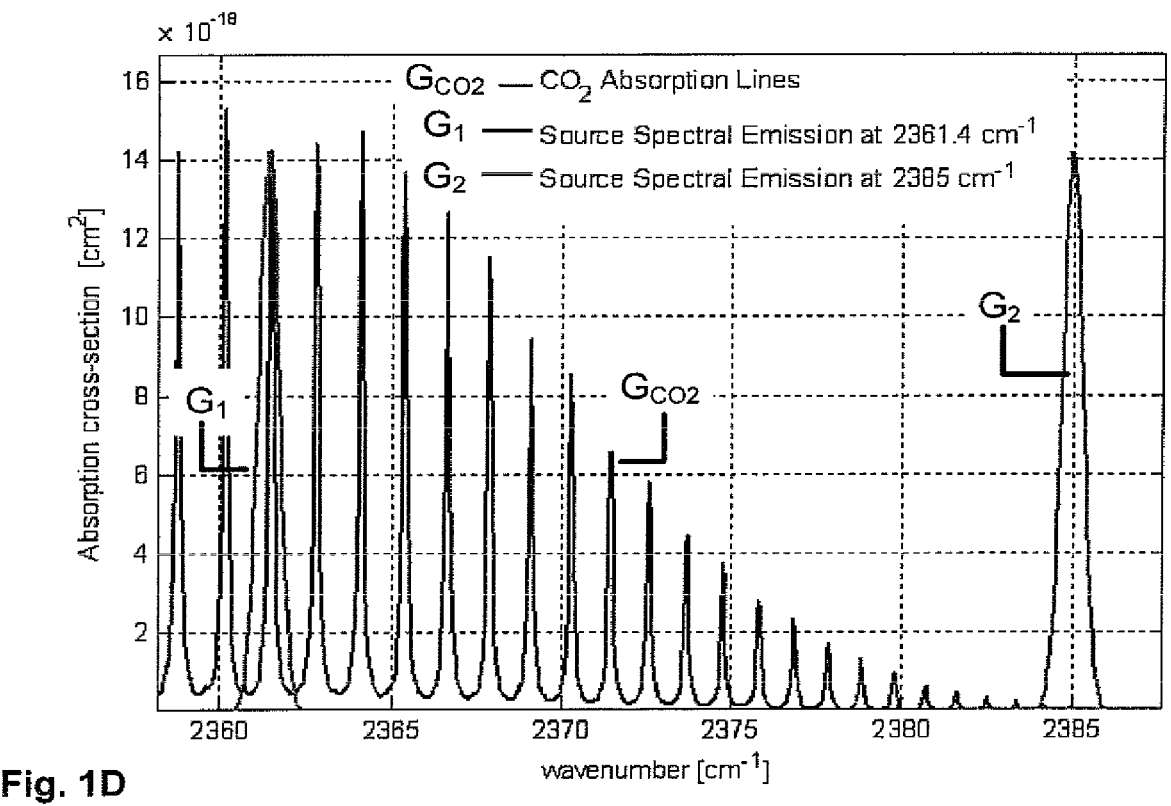

In this connection, reference is now made to FIGS. 1B, 1C and 1D, in which FIG. 1B shows a graph of the absorption cross section of $CO_2$ at ambient conditions (namely pressure of 1 atmosphere and temperature of 25° C.) as a function of wave number (taken from HITRAN database), and FIGS. 1C and 1D show in more details a part of this absorption cross section of $CO_2$ superposed with two examples of spectral emission profile of the light source for the first and second wavelengths produced by a QCL light source. These profiles correspond to substantially monochromatic light beams of first and second narrow wavelength spectra. In the example of FIG. 1C the emission profile of the light source for the first and second wavelengths respectively, overlap/cover an absorption peak (absorption line) of the $CO_2$ and overlap/cover an absorption valley (transmission line) of $CO_2$ in the mid-IR spectrum near 4.3 microns. In FIG. 1D, as in FIG. 1C, the emission profile of the first wavelength, overlaps an absorption line of the metabolic gas, while the second wavelength is located outside a spectral range of intense absorption lines of the metabolic gas.

More specifically FIG. 1B shows the features of the $CO_2$ absorption spectrum in wave-number range of near about 2300 to 2380 $cm^{-1}$ (i.e. for mid-IR wavelength range of about 4.2 to 4.35 microns).

FIG. 1C shows in more details the absorption spectrum (graph $G_{CO_2}$) of $CO_2$ in the wave-number range of about 2359 to 2364 $cm^{-1}$ (i.e. for wavelengths ranging between 4.230 to 4.239 microns) and illustrates the typical width of $CO_2$ absorption lines of about 0.07 $cm^{-1}$ (namely in the order of about 0.15 nm in that wavelength range).

FIGS. 1C and 1D present narrow spectral profile (graphs $G_1$ in these figures) of a first light beam (first type wavelength) produced by a tunable QCL light source 12 used in some embodiments of the present invention. The typical spectral width of the QCL emission is of full-width-half-maximum (FWHM) of about FWHM=0.7 $cm^{-1}$ (i.e. about 1.25 nm), and the figures show the spectrum of the light-beam being tuned to a central wave-number of 2361.4 $cm^{-1}$ (wavelength of about 4234.8 nm microns) corresponding to the maximum of one of the absorption lines of the $CO_2$ gas.

In the example of FIG. 1C the second wavelength presented by graph $G_2$ was tuned to central wavenumber of 2362 $cm^{-1}$ (wavelength of about 4233.7 nm) which is in the middle between the two absorption lines of the metabolic gas. Thus, in this case the $CO_2$ absorption at the second wavenumber will be much lower, than at the first one.

In the example of FIG. 10 the second wavelength presented by graph $G_2$ was tuned to central wavenumber of 2385 $cm^{-1}$ (4192.9 nm). Therefore in this example the second wavenumber is outside the spectral range/band of high absorbance by the metabolic gas (e.g. outside the so called 4.3 micron absorbance band of $CO_2$ at which main $CO_2$ absorption lines are present). Accordingly the $CO_2$ absorption at 2385 $cm^{-1}$ wavenumber is much lower, than its absorbance at both at the 2361.4 $cm^{-1}$ and 2362 $cm^{-1}$ wave-numbers.

Figure 1E:
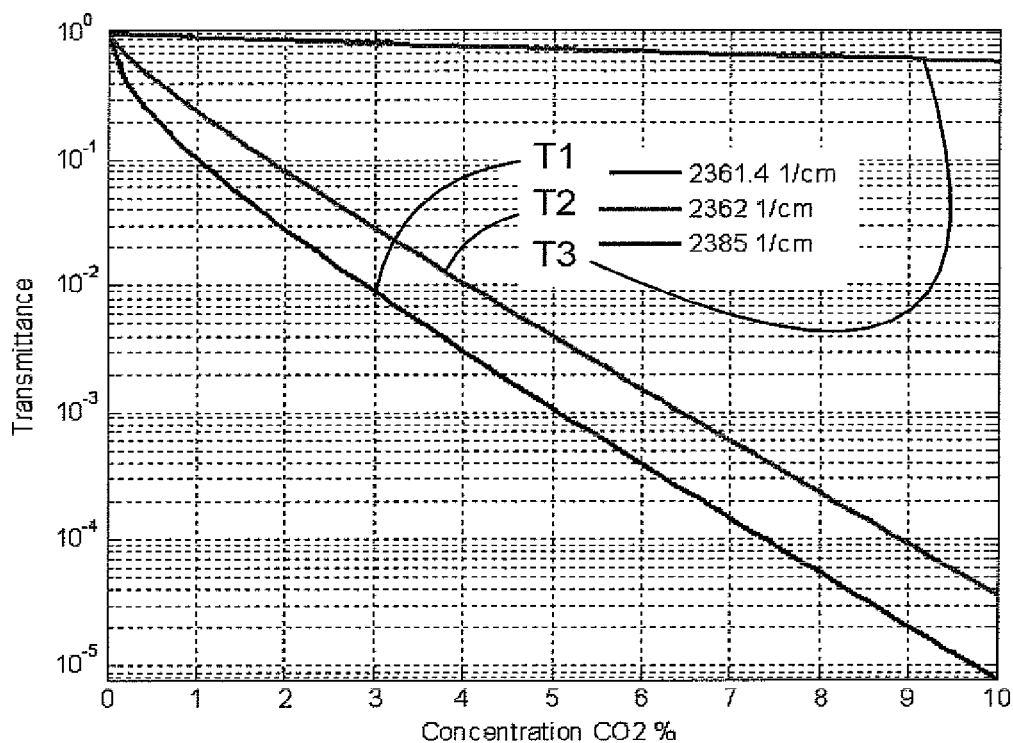
FIGS. 1E and 1F respectively show logarithmic scale graphs illustrating the transmittance of $CO_2$ for the first and second type wavelengths of FIGS. 1C and 1D, and a ration of the $CO_2$ transmission in these wavelengths.

The transmittance of $CO_2$ for the above exemplified wave-numbers of the first and second type wavelengths is illustrated in logarithmic scale in FIG. 1E for various concentrations of the metabolic gas $CO_2$. The transmittance was simulated for a container with transparent walls filled with mixed $N_2$ and $CO_2$ gases at different $CO_2$ concentrations, at normal pressure, normal/room temperature of 300 K, and with optical absorption path of 8 cm. The transmission of the first type wavelength (graph $G_1$ in FIGS. 1C and 1D corresponding to wave-number 2361.4 $cm^{-1}$) is illustrated in graph T1. The transmission of the second type wavelengths (graphs $G_2$ in FIGS. 1C and 1D) corresponding to wave-numbers 2362 $cm^{-1}$ and 2385 $cm^{-1}$ are illustrated in graphs T2 and T3 respectively. As shown from these graphs, the absorbance of the first wave-number in the $CO_2$ (graph T1) is substantially higher than the absorbance of the second type wave-numbers (graphs T2 and T3).

Figure 1F:
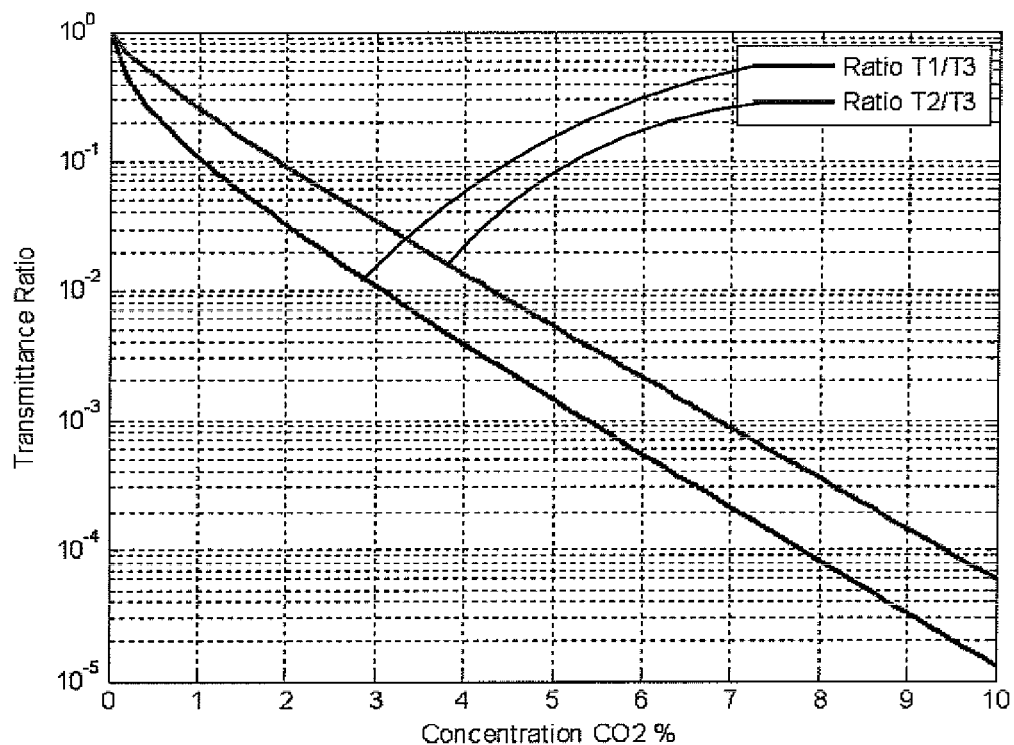

FIG. 1F shows in self-explanatory manner the transmittance ratios T1/T3 and T2/T3. These ratios are monotonically decreasing functions in both cases. Accordingly in some embodiments of the present invention it may be sufficient measure the $CO_2$ absorbance to obtain the value of one such ratio which is sufficient to for unambiguous determination of the $CO_2$ concentration in the container. However, in some embodiments of the present invention the reliability of the measurements are further improved by utilizing more than two wavelengths (e.g. to obtain more than one such ratio). That is especially relevant for high concentrations of $CO_2$ gas (exceeding few percent level) where absorption at certain wavelengths could be very strong and measured signal very weak.

To this end, according to the invention the controller operates/tunes the light source to emit light in the first substantially monochromatic wavelength(s) (e.g. as illustrated in graph $G_1$) corresponding and overlapping/covering the high absorbance peaks/lines of the metabolic gas such as those of $CO_2$ illustrated in the figure, thereby providing accurate measurement of the $CO_2$ absorbance. Additionally, as noted above, the controller operates/tunes the light source to emit light in second substantially monochromatic wavelength(s) (e.g. as illustrated in graphs $G_2$ of FIGS. 1C and 1D) corresponding to regions/valleys of low absorbance of the metabolic gas (e.g. transmission lines between the absorption lines which spacing is in the order of about 1 $cm^{-1}$ to 1.5 $cm^{-1}$-about 1.8 nm-2.5 nm in wavelength, and/or regions outside the high absorbance band of the gas). These second monochromatic wavelength(s), while being narrow and tuned so as to substantially not overlap with the absorption lines are provided for reference to the absorption of materials in the optical path other than the probed metabolic gas. Further, these second wavelengths are in the general neighborhood/band of the first wavelengths such that they provide reference data being indicative, with good accuracy, of the absorption of the first optical wavelength(s) in the optical path, in case the probed metabolic gas was absent there. In other words, the second predetermined wavelength is selected such that measured data of the transmission thereof provides reference indicative to the optical absorbance of the first wavelength by materials other than the metabolic gas.

For example, in some cases a spectral distance between a "first type" wavelength of the emitted light and a "second type" wavelength serving for the reference measurement (to which the metabolic gas is substantially transmitting) is in the order of 0.5 $cm^{-1}$-0.75 $cm^{-1}$ that corresponds to the half of distance between two absorption lines of $CO_2$ gas. Yet, in other case the separation distance can be of order 30 $cm^{-1}$ for the second absorption line to be outside the whole spectral range with intense absorption lines. In that case this wavelength could be used as reference wavelength transmittance of light beam at this wavelength does not depends on the concentration of $CO_2$, but rather reflects absorptions of the light beam on other optical components such as container walls transmittance. Hence, the spectral distance between the first and second wavelengths is substantially small such that the first and second wavelengths are characterized by same or similar transmission through predetermined/conventional materials used for conventional containers of biological material.

The use of such first type wavelength(s) for the measurement of absorbance by the metabolic gas and the second type wavelength(s) close thereto for reference measurements allows to detect small/minute changes in the metabolic gas concentration with high sensitivity and accuracy. For example changes of 10 ppm (or 0.001%), and even as low as 1 ppm (0.0001%) in the gas concentration can be detected even in relatively noisy environments in which various other materials such as those of the walls of the storage-bag and/or fermentation container and/or vapors (e.g. water vapors) are located in the region of interest. The effects of the later can be discarded with accuracy based on the reference measurements of the second wavelengths being close to the first wavelengths. Consequently, the present invention allows the detection of relative concentrations of metabolic gas from 0 to 100% (full dynamic range) using one single device having a sensitivity range of 1-100 ppm, preferably 1-10 ppm.

As a result of the above, in some cases the technique of the present invention is employed to measure metabolic gas concentrations in conventional containers such as conventional storage bags/vials for platelets. This is achieved by taking advantage of the above described technique utilizing the "first type" and "second type" (measurement and reference wavelengths) in the spectroscopic measurements. Thus, the detection of various microorganisms in-situ in such conventional and generally arbitrary containers is made possible although the materials of the container is not a-priory known, and although the container's materials may include materials such as polymers and/or other materials, which may be relatively opaque to the IR wavelengths used by the system of the invention (e.g. opaque to wavelengths in the mid-IR).

As noted above in some embodiments the detection module 15 includes an electronic signal processor/lock-in amplifier 13 that receives the signal from the IR detector 14. Use of the lock-in amplifier enables to even further improve the signal to noise ratio (SNR) provided by the system thus further improving the sensitivity and accuracy of the measurements relating to the concentration(s) of metabolic gases and consequently detection of microorganisms. To this end, in such embodiments the control system 30 is adapted for operating the tunable broadband IR light source 12 for applying time modulation to intensity of light emitted in one or more (e.g. in each) of the at least two (first and second) wavelengths, and also operating the lock-in amplifier 13 to determine/measure the detected intensity(ies) of the emitted light with high accuracy based on that modulation. Accordingly, transmittance of the region of interest to the first and second wavelengths (e.g. to all wavelengths used in the measurement) can be determined with high accuracy based on the intensity modulation, while noise is mostly discarded as it is generally not modulated in the same way. It should be noted that the configuration and operation of various lock-in amplifiers are generally known in the art of signal processing and are therefore not specifically described herein. A person versed in this art would readily appreciate the various possible configurations of such lock-in amplifier with appropriate modulation to the emitted illumination to be used in the system of the invention.

In some embodiments, the system 10 is configured and operable for utilizing its ability to accurately detect small changes in the metabolic gas concentration, for operation in-situ and/or in real time to non-invasively detect microorganisms in the containers/bags permeable to the metabolic gas and/or in association with one or more openings (inlets/outlets) through which in/out flow of gases may occur. Specifically, in some embodiments, after analyzing the concentrations of the metabolic gas in the dead space 28, the controller 30 is adapted for further processing the concentration of metabolic gas to detect microorganisms in the biological material 26.

In some cases, the detection is merely qualitative to identify whether significant levels/amounts of such microorganisms exist in the biological material 26. In other cases, the detection is qualitative and is aimed at estimating the levels (e.g. amounts/concentrations) of the microorganisms in the biological material 26.

In some embodiments the system is adapted/configured for operating in closed containers, sealed and non-permeable to the probed metabolic gas(es). In such cases, the concentration of the metabolic gas in the container is a function of the time the container is sealed and the amount of microorganisms therein during that time. Specifically, in sealed container the concentration of $CO_2$ is increasing function with time as long as there is biological activity inside of container responsible for $CO_2$ emission. Thus, the concentration of living cells in that case depends on the growth history of the cells from the beginning of incubation. The correspondence between the number of cells and measured $CO_2$ concentration could be find out in that case by computing rate of changes of $CO_2$ concentration and correlating it with respiration rate of a single cells and the number of cells.

Alternatively or additionally, in some embodiments the container is not sealed with respect to the metabolic gas. For example, in cases of monitoring a biological material stored in bags or storage vials for blood components, which are permeable to the metabolic gas, and/or in cases of monitoring a biological material in fermentation containers associated with gas inlet(s) and/or outlet. Advantageously, the present invention allows for detecting microorganisms also in such containers in-situ and in real time without taking and sealing a sample of biological material from the containers and without incubating the sample (i.e, non-invasive detection). This is performed by taking advantage of the high sensitivity and accuracy of the technique of the invention for detecting small changes in the metabolic gas concentration.

To this end, the controller 30 system may operate to measure the metabolic gas concentration in a dead space associated with the container of biological material, while the dead space is non sealed to the metabolic gas, and to utilize the measured concentration of the metabolic gas to detect the microorganisms qualitatively and/or qualitatively based on an equilibrium condition (e.g. balance/difference) between a rate of escape/flow of the metabolic gas from/into the container and a rate of generation or consumption of the Metabolic gas by the microorganisms.

In cases the container is permeable to the metabolic gas, processing may be performed by computing/estimating the microorganisms level in the biological martial 26 based on the measured concentration of the metabolic gas diffusion of that gas through walls of the container 24. In this case, the container may be a conventional storage container for platelets or other blood components.

Additionally or alternatively system 10 allows real-time in-situ detection of microorganisms in biological material 26 contained in fermentation container 24 (e.g. in a container of a fermentation system). To this end, the controller 30 may be configured and operable to determine the level of microorganisms based on the equilibrium condition (e.g. balance/difference) between the rate of escape/flow of the metabolic gas from/into the container 24 through an outlet thereof, and a rate of generation or consumption of the metabolic gas by the microorganisms. For example that balance may be determined based on a difference between concentrations of the metabolic gas in a gas inlet to the container 24 (e.g. the concentration in the external atmosphere) and a concentration of that metabolic gas in the atmosphere in the dead space 28 of the container, which may be a dead space of the container itself (e.g. above the biological material 26) or a dead space in fluid communication therewith, for example located at a gas outlet of the container. The difference in the metabolic gas concentrations corresponds to the amount of microorganisms in the container. More particularly, this is the difference that may be computed from the difference in the amount of metabolic gas flowing in and out of the container (e.g. computed by the controller 30 as the difference between the products of the flow rates in the gas inlet and outlets multiplied by the metabolic gas concentration thereat respectively).

The controller 30 may utilize predetermined data of the concentration of the probed metabolic gas in the gas inlet (e.g. in the external atmosphere of the container. Also the spectroscopic/optical measurements may be applied to a region of interest associated with the cavity/dead-space of the container itself and/or at a gas outlet from the container. The light source 12 and the detector 14 may be optically coupled to one or more optical windows exposing the dead-space to be inspected (e.g. optical windows coupled to the fermentation container and/or to gas outlet).

In some embodiments of the present invention, the system 10 is specifically configured for real time and continuous/periodical monitoring of fermentation processes. In such embodiments the controller 30 may be adapted to apply continuous/periodic detection of microorganisms and/or their level in the fermentation container. In this connection, the controller 30 may be adapted to repeatedly operate the optical system in the manner described above to obtain, in real time, and/or repeatedly within predetermined time intervals, data indicative of the metabolic gas concentration in the container and/or in its outlet. Repeatedly/continuously obtaining such gas concentration during a period of time provides indication to the amount of microorganisms in the container as a function of time and/or indication to the change/rate of change in this amount. The controller may be adapted to process the data indicative of the amount of microorganisms, or the change thereof, as function of time for monitoring and/or controlling the fermentation process occurring in the container. For example, reference data/model relating to the fermentation process in a container may be utilized by the controller to determine actions/operations to be carried out for controlling the fermentation (e.g. stopping the fermentation and/or changing some of the fermentation conditions such as temperature and/or other conditions). This reference data may for example be stored in the form of a lookup table (LUT) and/or a set of one or more functions/models relating to the amount of microorganisms and/or rate of change in their amount with certain actions to be carried out and/or certain fermentation conditions to be applied/maintained.

The fermentation process monitoring/controlling can be realized using a model (e.g. mathematical-model/formula and/or data) relating the amount of biomass in the fermentor with measured concentration of $CO_2$. The model may be pre-determined and predefined in advance and loaded to memory and/or other storage device of the controller 30 in the form of data/LUT and/or as a set of instructions soft/hard coded.

Such a model relating the amount of biomass in fermentor with the concentration of $CO_2$ may be obtained/determined in advance by utilizing various techniques. For example, the amount of biomass may be measured by optical density techniques (OD) and/or viable counts and/or other run parameters such as pH, RPM, TEMP, and the total volume (TV) of the metabolic gas $CO_2$ emitted/consumed by the microorganisms from the beginning of the run (seeding time). The model may be a mathematical model based for example on multivariable robust regression analysis. Verification of the mathematical model may be performed by number of fermentation processes performed under same conditions, which are optimal for the high product yield in the batch fermentor.

A RUN protocol, such as executable instructions and/or LUT, is then used by the controller 30 for estimating, the amount of biomass in the fermentor based on the model's parameters and the real-time measured concentration of $CO_2$ gas and possibly other run parameters. The RUN protocol is based on estimated values of the biomass and may include data indicative of different aspects/actions to be taken during the monitoring of the fermentation process (e.g. conditions for adding nutrients for cell in fermentation, determining optimal inducing time (for recombinant protein production) and harvesting time, controlling pH level and other run aspects.

As noted above, in cases of biological containers which are not-sealed to the metabolic gas (e.g. permeable containers or containers of fermentation), the bacterial growth will be reflected in real time in changes in the metabolic gas concentration. For example, in case the bacteria are no longer alive, the carbon dioxide concentration will be substantially equal to equilibrate with that in the air outside the storage tank.

The concentration of metabolic gases inside a gas permeable container is determined by equilibrium conditions between release and rate of diffusion of metabolic gases through the walls of the container. It should be noted that in the following description containers permeable to the metabolic gas(es) are considered as an example of not-sealed containers with respect to the metabolic gas(es). Also, in the description below such permeability and diffusion of the gas from and into the container is exemplified as relating to the permeability of the container's walls. However, it should be understood that the technique described below is applicable to any other type of containers no sealed with respect to metabolic gases, wherein the flow in and out of the container may be additionally or alternatively through gas inlets and/or outlets of the container. Further, in connection with the diffusion equations used in the description below, it should be noted that in case of non-permeable non-sealed containers these can be substituted by proper equations taking into account other "diffusion" paths such as flow through inlet/outlet pipes and concentration of the metabolic gas therein. In other words, although the examples in the description below mainly refers to permeable platelets bags, it should be understood that the technique can easily be generalized by a person versed in the art for other types of cavities where metabolic gas may be concentrated, including the dead space in the container itself and/or that of the inlet/outlet pipes of a fermentation container for example.

The equation for gas (such as $CO_2$) production and transport through the walls of a permeable container states:

$$\frac{\partial m_{CO2}}{\partial t} = -JA + W \quad (1)$$

where $m_{CO2}$ is the mass of $CO_2$ gas inside the container, J is the diffusion flux from the walls of the container in units kg/(s·m²), A is the surface of the walls exposed to the gas exchange and W is the source term that describe total rate of $CO_2$ production inside the container. W has units of kg/s. The diffusion flux is given by equation 2:

$$J=(\rho_{CO2}(t)-\rho_{CO2}^D)\nu \quad (2)$$

where, $\rho_{CO2}(t)$ is the mass concentration of the $CO_2$ gas in units kg/m³, measured at time t, $\rho_{CO2}^0$ is the ambient mass concentration of $CO_2$ gas, $\nu$ is the membrane permeability coefficient in units m/s.

In equilibrium $$\frac{\partial m_{CO2}}{\partial t} = 0,$$

meaning that the $CO_2$ emission rate of enclosed biological material is equal to the total diffusion rate through the container walls:

$$W(t)=(\rho_{CO2}(t)-\rho_{CO2}^0)\nu A \quad (3)$$

If the container is sealed, then this equation is inapplicable, since no gas exchange can undergo through the container walls. In this case, the concentration of $CO_2$ is gathered by Eq. (1) with the first term in the right side equal to zero:

$$\frac{\partial m_{CO2}}{\partial t} = W \quad (4)$$

where W(t) is the $CO_2$ emission rate of enclosed biological material in units kg/s measured at time t. Taking into account that mass concentration is defined as the mass of a constituent divided by the volume $\rho_{CO2}=m_{CO2}/V$, the following expression is obtained for $\rho_{CO2}$ by integrating Eq.(4):

$$\rho_{CO2}(\tau) = \frac{1}{V}\int_0^\tau W(t)dt \quad (5)$$

where V is the volume of the container. Since, W(t) is nonnegative, $\rho_{CO2}(t)$ is monotonically increasing function with time. Time t=0 in the integral corresponds to the beginning of the run (seed time in the fermentation process). From the above equation, the following expression can be obtained for mean (W(t)) $CO_2$ emission of enclosed biological material averaged over time interval r:

$$\langle W(t)\rangle = \frac{(\rho_{CO2}(t) - \rho_{CO2}(t-\tau))V}{\tau} \quad (6)$$

The change of concentration $n_{CO2}$ can be measured by means of IR absorption of beam of tunable IR light source such as Quantum Cascade Laser directed through the container walls. As described above, the use of the tunable source instead of the fixed wavelength source allows direct measurement of $CO_2$ concentration inside the container regardless of container material and without use of etalon container.

The following are some examples of the technique of the present invention for detection of metabolic gas(es) concentration, assume that the container walls are at least partially transparent at the mid-IR frequency range where strong absorption of $CO_2$ occurs (around 2260 cm⁻¹-2390 cm⁻¹), and that the path for optical beam in the gaseous atmosphere inside the container is provided.

The dependence of % $CO_2$ level on the increase of bacterial contamination was studied experimentally. *Staphylococcus epidermidis* obtained from the American Type Culture Collection (ATCC) were used to contaminate a bag of platelets that were collected from a single donorby apheresis. The bacterially inoculated apheresis platelets were agitated at 22° C. and measurements were performed using QCL spectroscopy. The platelet container was measured before and during bacterial contamination. Samples were taken from the contaminated platelet bag and a standard culture plate count was used for determining bacterial concentration [colony forming unit (CFU)/mL] in the platelet medium.

Figure 3:
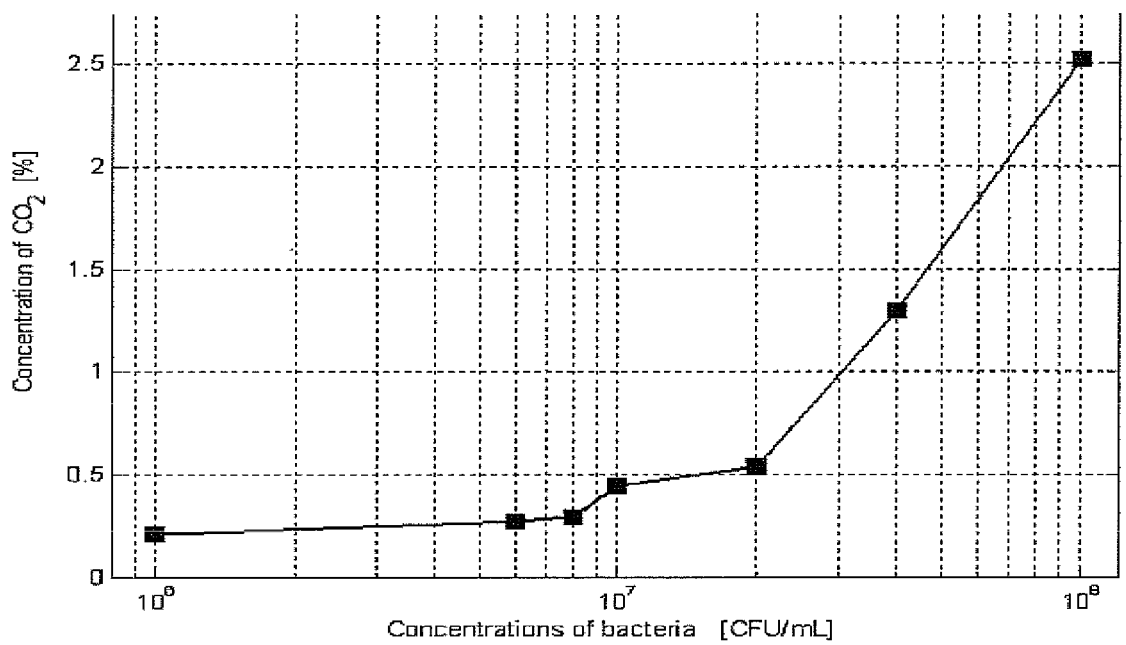
FIG. 3 shows the experimental results for a measured plot of % $CO_2$ vs. bacterial concentration.

Referring now to the drawings, FIG. 3 is a plot of % CO2 vs. bacterial concentration. The bacterial concentration that was measured at the point where % CO2 started to rise was between 1*10⁶ CFU/mL to 6*10⁶ CFU/mL, The Y-axis shows % CO2 level and the X-axis shows bacterial concentration measured using standard titration analysis.

Turning back to FIG. 1A, system 10 of the present invention may be used for measuring the concentration of carbon dioxide in the dead space 28 above the platelets 26 in a gas-permeable bag 24 that has been removed temporarily from storage and agitation for the purpose of measuring the concentration of carbon dioxide in dead space 28. The tunable infrared laser 12 (for example a QCL) and an infrared detector 14 are positioned so that the light beam 20 from laser 12 is aimed at detector 14. In this example, the light beam 20 is focused on detector 14 by a calcium fluoride lens 18. Bag 24 is positioned between laser 12 and detector 14 so that light beam 20 traverses dead space 28. Controller 30 tunes laser 12 to emit light beam 20 at selected wavelengths in the vicinity of 4.3 microns at a pulse repetition rate of 5 KHz, receive the corresponding response signals from detector 14, and analyze those signals to estimate the concentration of carbon dioxide in dead space 28. As noted above, the signal reception and analysis portion of the controller 30 may be implemented by a lock-in amplifier that locks onto the 5 KHz signal from detector 14 and displays the amplitude and phase of that signal. For an accurate measurement of the concentration of carbon dioxide in dead space 28 the path length of light beam 20 across the interior of bag 24 is preferably at least several centimeters.

Figure 2A:
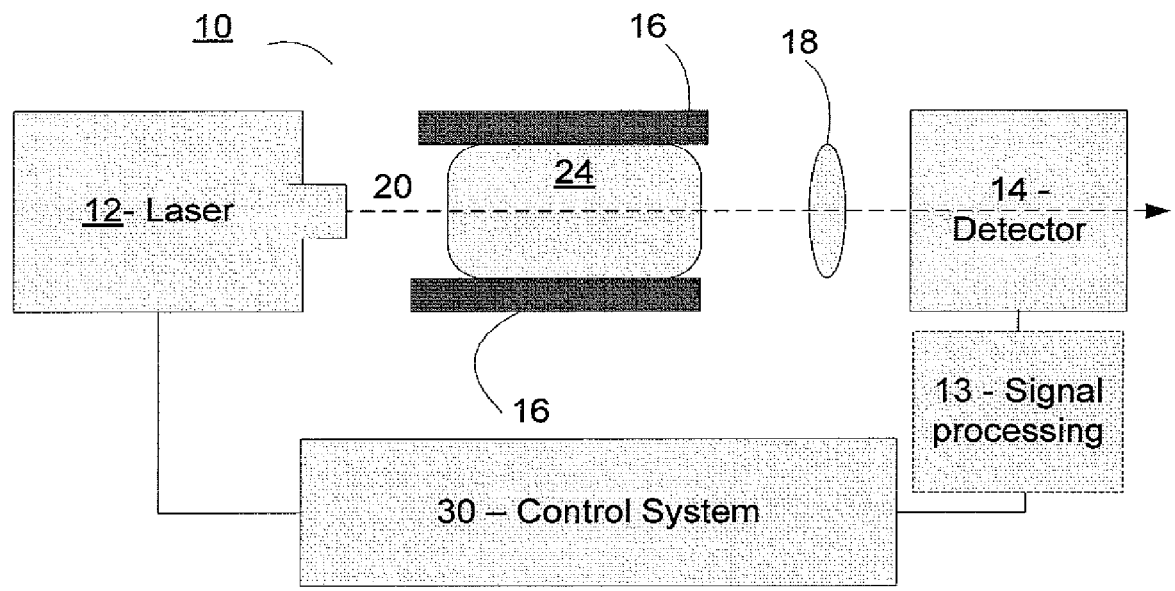
FIGS. 2A and 2B exemplify a system for detecting microorganisms in biological material utilizing a separate closed gas chamber connected to a container of biological material.
Figure 2B:
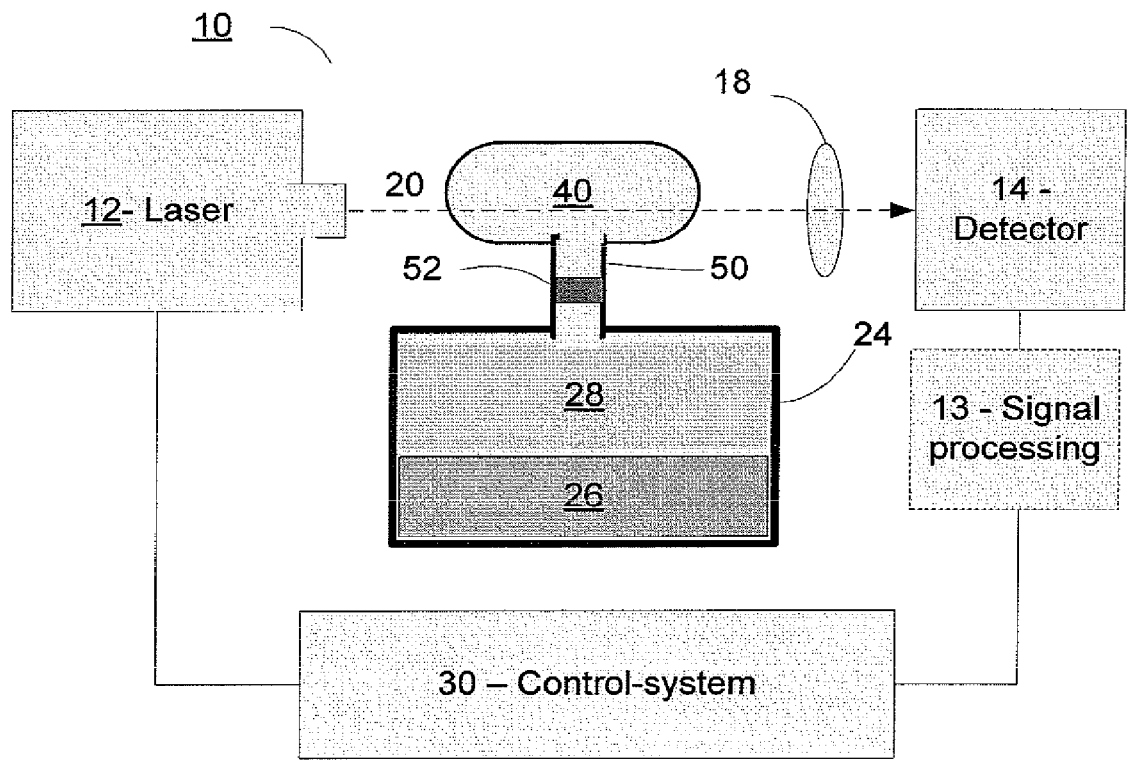

In practice, a sufficiently long optical path through bag 24 may not be available, and/or the walls of bag 24 may not be sufficiently transparent at the relevant wavelengths to allow an accurate measurement of the concentration of carbon dioxide in dead space 28. In this connection, reference is made to FIGS. 2A and 2B illustrating two modified configurations of system 10 that deal with these problems. System 10 is configured generally similar to that of FIG. 1A. As shown in FIG. 2A, the bag 24 may be held in place by two vertical walls 16. In distinction to the system of FIG. 1A, in FIG. 2B a separate closed (e.g. cylindrical) gas chamber (pipe/reservoir) 40 is used and is connected to the bag 24 using a connecting tube 50 which is by its one end connected by fusion with a heating instrument to the bag, as is routinely done to platelet bags in blood banks, for various reasons of their own. Such procedures are performed routinely without damaging the platelet bags or introducing contamination. The other end of the connecting tube 50 is connected to the chamber 40 that is at least partially transparent in at least a portion thereof to the relevant wavelengths and that is sufficiently rigid and long enough to provide a predetermined fixed optical path (e.g. of several centimeters) for light beam 20. In this specific but not limiting example, a filter 52 is used in tube 50, that is permeable to gases but not to liquids, and thus keeps liquids from bag 24 out of reservoir 40 but allows the gaseous contents of reservoir 40 to equilibrate with the gaseous contents of dead space 28 in the bag 24 so that the concentration of carbon dioxide in reservoir 40 is substantially identical to the concentration of carbon dioxide in dead space 28. The equilibration of the concentration of carbon dioxide between reservoir 40 and dead space 28 occurs sufficiently fast such that no special steps are needed to hasten this equilibration. Effectively, the interior of reservoir 40 is an extension of dead space 28. Such connection to the separate gas chamber may be used in case the required optical path (for detection of the specific metabolic gas) inside the container is unavailable and/or in case the container's walls totally block the IR radiation.

In a general case, irrespectively of whether the container is sealed or permeable with respect to the metabolic gases to be detected, the following technique may be carried out by the controller 30 for accurate, in-situ real time determination of the metabolic gas(es) concentration. IR transmission through the dead space in two or more wavelengths (comprising the above described first and second wavelengths) is measured as described above. The measured data is processed by the controller 30 for example by utilizing an absorption model of the at least one metabolic gas. To this end, a best fit between intensity values obtained from the absorption model and the measured intensity values is performed to thereby determine the concentration of the at least one metabolic gas.

The following is a not limiting example of the mathematical description of the measurement procedure of metabolic gas concentration inside a container using tunable IR light source.

The transmitted laser light intensity $l(\lambda_0)$ measured on the detector is given by at the laser central wavelength $\lambda_0$ is given by $$l(\lambda_0) = \eta l_0 \int_{\lambda_{min}}^{\lambda_{max}} f(\lambda - \lambda_0) e^{-\alpha_\lambda(cl + c_0 l_0)} d\lambda \quad (7)$$

where $l_0$ is the laser intensity, $\eta$ is the total intensity loss that are not related to optical gas absorption, $\alpha_\lambda$ is the absorption coefficient (in $cm^{-1}$) at the given wavelength of the light $\lambda$, c is the probed gas concentration (by volume) inside the container, $c_0$ is the concentration of the probed gas outside the container in the atmosphere, l is the pathlength inside the container, $l_0$ is the pathlength outside the container between IR source and detector, $f(\lambda - \lambda_0)$ is the laser spectral distribution function around the central wavelength $\lambda_0$.

The integration limits $\lambda_{min}$ and $\lambda_{max}$ with $\lambda_{min} < \lambda_0 < \lambda_{max}$ are assumed to be such that $f(\lambda)$ is nearly zero outside the integration domain.

The absorption coefficient $\alpha_\lambda$ can be calculated as:

$$\alpha_\lambda = n\sigma(\lambda) \quad (8)$$

where $n = P/k_B T$ is the concentration of molecules and $\sigma(\lambda)$ is the absorption cross section in $cm^2$. The signal on the detector is assumed to be proportional to the transmittance intensity. In case of tunable laser the central wavelength can be changed within certain range.

Thus, a model $S(x, \lambda l)$ for a signal on the detector can be written as $$S(x, \lambda_i) = b \int_{\lambda_{min}}^{\lambda_{max}} f(\lambda - \lambda_i) e^{-\alpha_\lambda(x + c_0 l_0)} d\lambda \quad (9)$$

where $x = cl$ and b is a constant, x (and therefore c) can be found from equation (11) if the measurement is done at two or more wavelengths of light $\lambda$. In that case the unknown constant b can be excluded from the set of equations.

The concentration c can be determined from n measured values of the signal $S_i, i = 1, \ldots, n$ at different wavelengths $\lambda$ by utilizing nonlinear minimization of the model $S(x, \lambda i)$ as provided by function s(x) below:

$$s(x) = \sum_{i=1}^{n-1} \left[ \log\left(\frac{s(x, \lambda_i) + \epsilon}{s(x, \lambda_n)}\right) - \log\left(\frac{s_i + \epsilon}{s_n}\right) \right]^2 \quad (10)$$

where $\epsilon$ is a noise level at the detector. s(x) is essentially least squire norm of the logarithm of the ratio between measured and theoretical signals $S_i$ and $S(x, \lambda i)$ at wavelength $\lambda i, i = 1, \ldots, n-1$ and the signal at $\lambda_n$. Thus, $\lambda_n$ is used as a reference wavelength for $\lambda i, i = 1, \ldots, n-1$. The parameter E insures that function s(x) is not singular if one of $Si = 0$. From equation (9) the concentration c can be determined, provided that the optical path length l is known.

The following is a specific example for using the technique of the invention for $CO_2$ absorption simulations and evaluation. The simulations of $CO_2$ absorption within plastic bags were performed using HITRAN database of $CO_2$ line intensities at ambient conditions and are described above with reference to FIGS. 1B and 1C.

Figure 4:
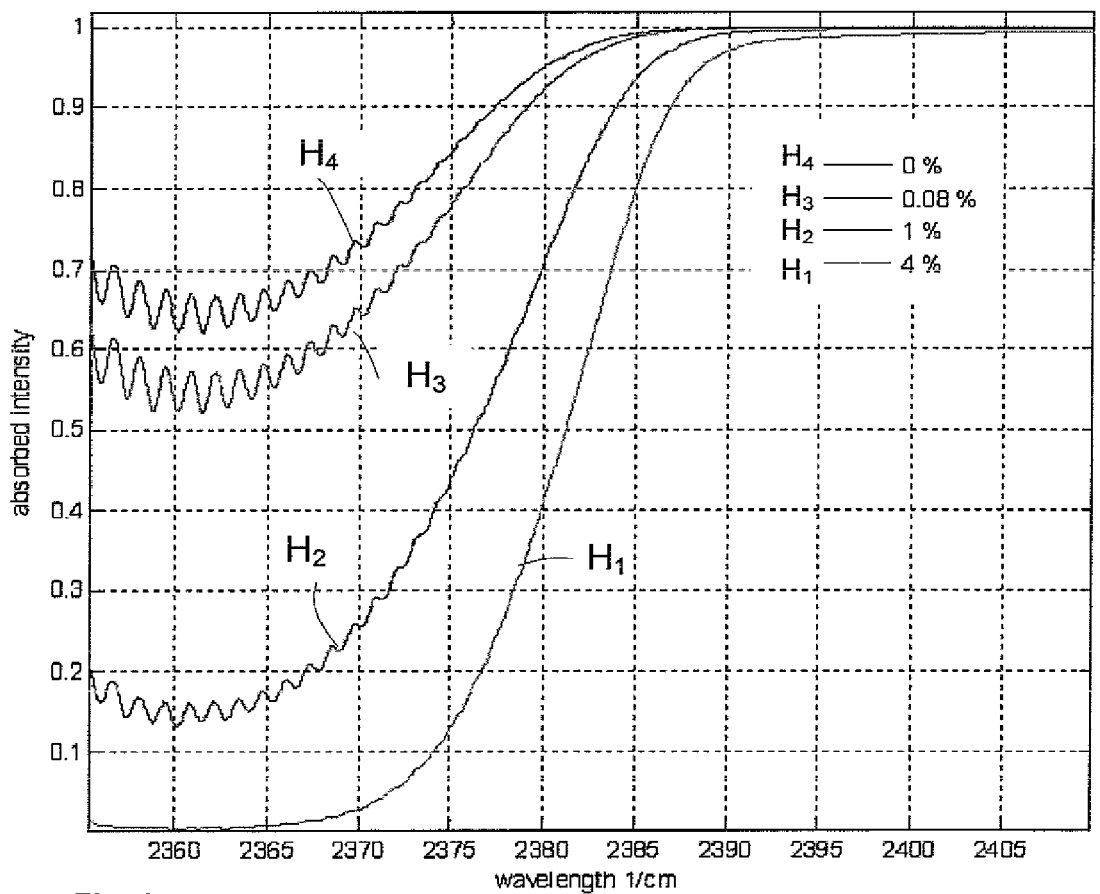
FIG. 4 shows simulated absorption versus wavelength and CO2 concentrations of the beam of the QCL in the IR spectral range 2355 $cm^{-1}$-2410 $cm^{-1}$.
Figure 5A:
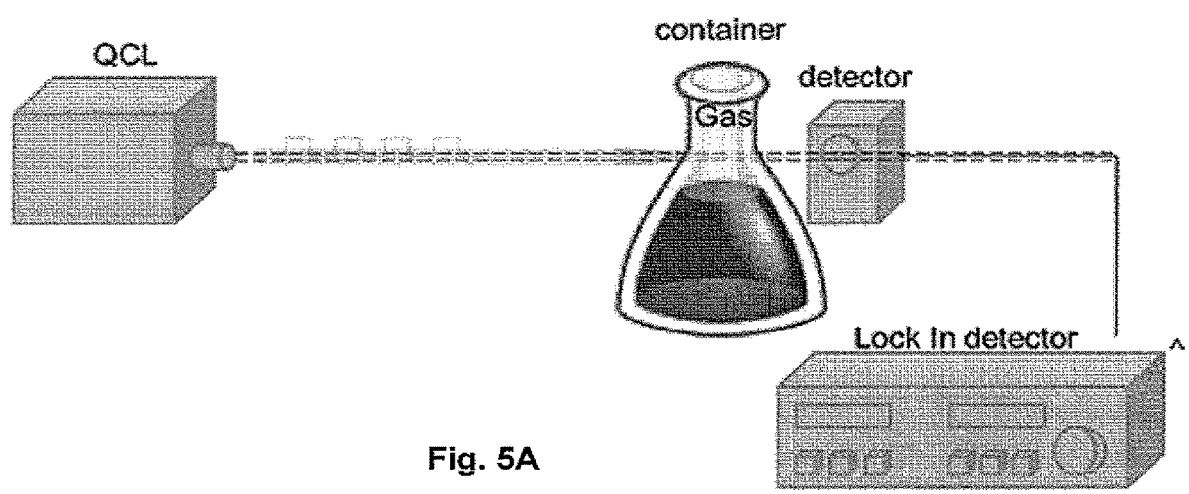
FIGS. 5A and 5B show experimental set ups of a system used for detection of metabolic $CO_2$ inside a platelets product in a plastic bag utilizing direct measurement through the bag containing the platelets (FIG. 5A) and utilizing a separate gas chamber connected to the platelets container (FIG. 5B)
Figure 5B:
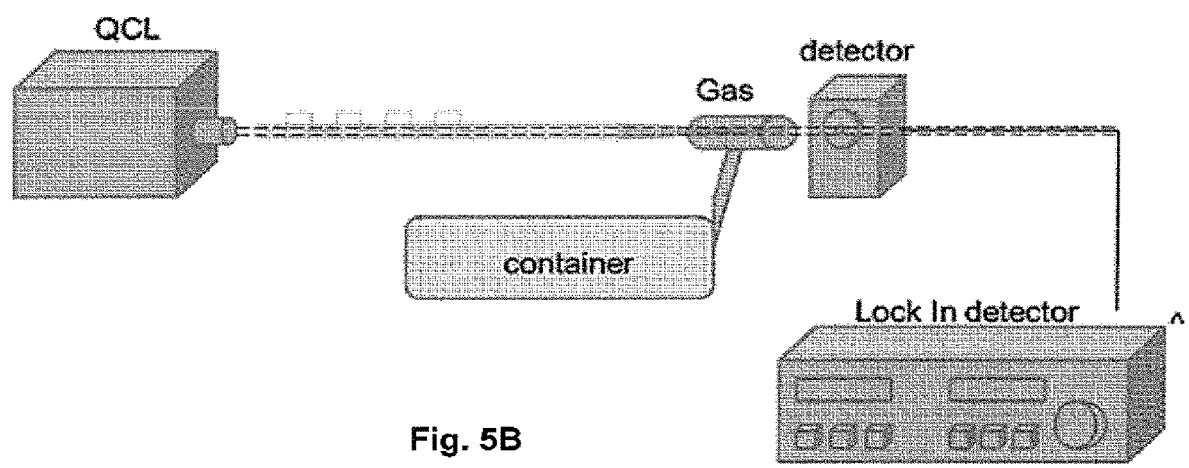

FIG. 4 shows simulated absorption versus wavelength and $CO_2$ concentrations of the beam of the QCL calculated using equation (7) in the IR spectral range 2355 $cm^{-1}$-2410 $cm^{-1}$. The graphs $H_1$, $H_2$, $H_3$ and $H_4$ correspond to the absorbed intensities for respectively 4%, 1%, 0.08% and 0% of the $CO_2$ concentration. As shown, the graphs have smooth behavior of the spectra on wavelength and the transmittance increases when light frequency changes from 2360 $cm^{-1}$-2410 $cm^{-1}$ Reference is made to FIGS. 5A and 5B showing experimental set ups of the system of the present invention for detection of metabolic $CO_2$ inside a platelets product in a plastic bag utilizing respectively direct measurement through the bag containing the platelets (FIG. 5A) and utilizing a separate gas chamber connected to the platelets container (FIG. 5B). As shown in the figures in a self-explanatory manner, the set up utilizes tunable QCL, IR detector (e.g. equipped with a CaF2 plano-convex lens), lock-in amplifier detector and a controller. The QCL operates in the pulse mode with repetition frequency of 5 kHz and pulse width 500 nsec. The tunability range of the QCL includes the measurement range that was from 2361.4 $cm^{-1}$ till 2391 $cm^{-1}$. The procedure for determination $CO_2$ concentration within container may thus be as follows: the light beam is transmitted from the QCL through a small container connected to the plastic bag, container as shown in FIG. 2B described above. Signal on IR detector is measured at different wavelengths of light $\lambda i$ $i = 1, \ldots, n$ in the range from 2361.4 $cm^{-1}$ till 2391 $cm^{-1}$. The concentration c of $CO_2$ gas inside the container is estimated using equation (10) for different using the nonlinear minimization of the function s(x).

As noted above in embodiments of the present invention configured for monitoring and/or controlling fermentation processes, the monitoring and controlling of the fermentation may be based on a model such as formula and/or reference data relating various parameters of the fermentation including metabolic gas concentration with an estimation of the biomass (i.e. it amount) in the fermentation. In some cases a Linear Regression Model is used for estimating the biomass during the fermentation process.

In this connection, the regression model may be pre-computed model calculated utilizing statistical regression analysis for modeling the relationship between one or more parameters, also considered as to as predictor x and/or regressor variable(s), and one or more other parameters, also referred to as response variable(s) y.

For the case of estimating of biomass in the fermentation, the regressor/predictor variable(s) (generally denoted herein $x_i$) include the concentration C of $CO_2$ measured in the gases emitted from the fermenter, and/or TV being the Total Volume of $CO_2$ emitted from the beginning of the run (seeding time). The response variable (generally denoted herein y) may include the optical density OD of the biological material in the container and l or the viable count VC (namely a measure of the count of microorganisms as typically obtained via microscope count). In cases that multiple linear regression model is used the response variables—generally noted y are related to k repressor's, $x_1$, $x_2$, ..., $x_k$ according to the following formula:

$$y = \beta_0 + \beta_1 x_1 + \beta_2 x_2 + \ldots \beta_k x_k + \in \quad (11)$$

where $\beta i$, $i=0, \ldots, k$, are model parameters (e.g. coefficients of the model), $x_i$ are the regressor/predictor variable(s) (e.g. parameters of the fermentation process which are independent from the response variable (OD in this case)), and e is the random components with supposed mean zero and variance $\sigma^2$.

The regressor/predictor variable(s) $x_i$ may be measured in real-time during the fermentation process (e.g. without sampling/extracting the material from fermentor and probing). For example, the total volume (TV) of $CO_2$ gas emitted by microorganisms vs. time may be calculated using the formula:

$$TV(t) = \int_o^t \text{rate} \times c(t) dt \quad (12)$$

where TV (t) (in liters) is the total volume of $CO_2$ gas emitted by the species since the beginning of the run (from the beginning of the fermentation process), rate is the aeration rate (e.g. measured in liters/min), and c(t) is the concentration of $CO_2$ (in volume fraction) measured in emission gases from the fermentor.

In this connection, it should be understood that according to some embodiments of the present invention, in addition to the $CO_2$ concentration predictor parameter c(t), in some cases other run/predictor parameters/variable(s), may also be measured (e.g. continuously) to provide estimation of the response parameter(s) y with improved accuracy. To this end the generalized formula (13) above may be used as a model defining the relation between the predictor parameters measured/considered $x_i$ and the response parameters y. For example the predictor parameters $x_i$ may include:

RPM—agitation rate in fermentor (e.g. provided as an input from a controller controlling the operation of the fermentation system);

RATE—aeration rate measured in liters/min (e.g. measured at the inlet and/or outlets from the fermenter);

pH—acidity level in fermentor (e.g. measured by pH electrode in the fermenter)

DO—dissolved oxygen $dO_2$ (e.g. measured by dissolved oxygen probe in the fermenter)

Figures 6A, 6B:
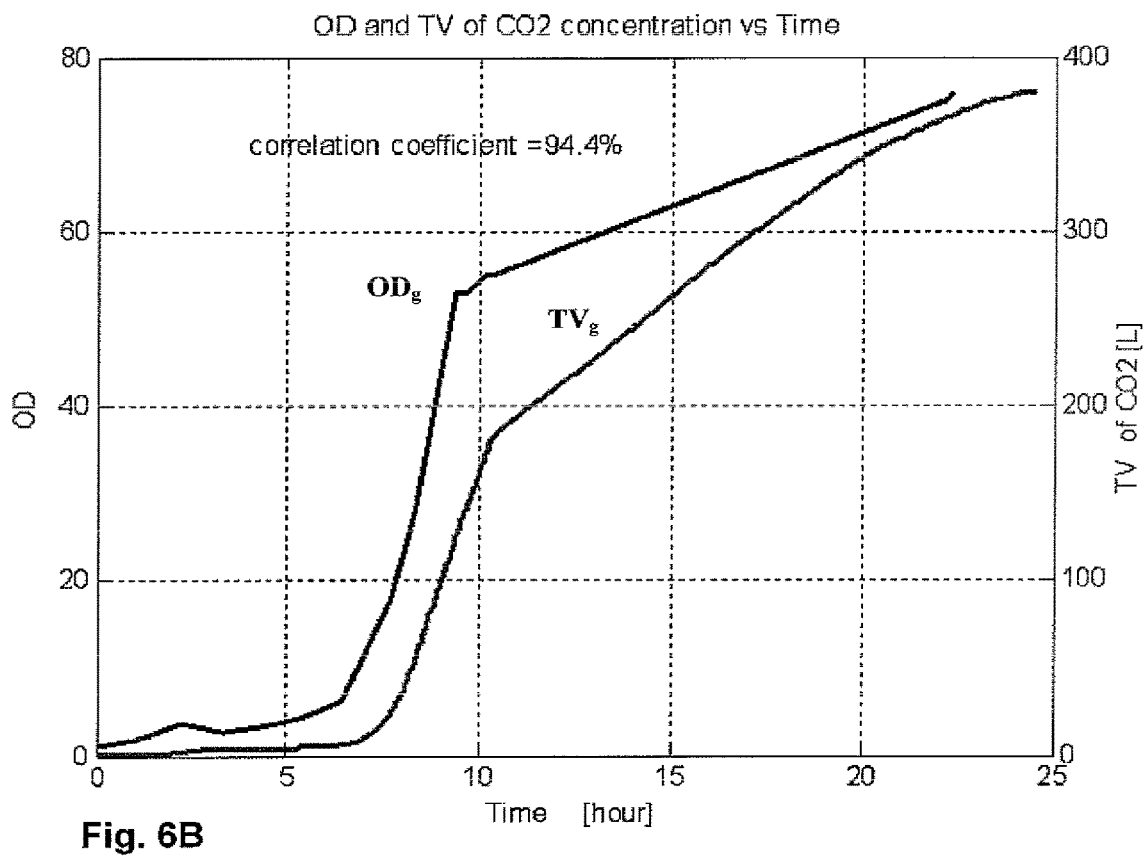
FIGS. 6A to 6D show experimental results for a fermentation process/run of recombinant protein production utilizing *Escherichia coli* E. CO fermentation.

Temp—temperature in fermentor,

FIG. 6A is a table illustrating several of the above predictor parameters measured/obtained during an experiment of a fermentation process/run of recombinant protein production utilizing *Escherichia coli E. Coli* fermentation. The recombinant proteins are widely used in biotechnology and medical applications as vaccines and protein therapeutics, and as industrial enzymes for detergents and fuel ethanol production. Such recombinant protein products are made by inserting the gene that encodes the desired protein into a host cell (bacteria, yeast, insect, or animal cells) capable of producing this protein. FIG. 6B shows graphs $OD_g$ and $TV_g$ illustrating respectively the measured optical density—OD and the total volume of $CO_2$ emission-TV, as a function of time. OD and TV were measured during a fermentation experiment. As shown the OD is increased from 1 to about 55 during the first 10 hours of the experiment. Then it gradually continues to grow up to values of 75 during the next 12 hours of experiment. TV was measured continuously while OD at 15 time points as specified in the table in FIG. 6A. The correlation coefficient between OD and TV is 94.4%.

Figure 6C:
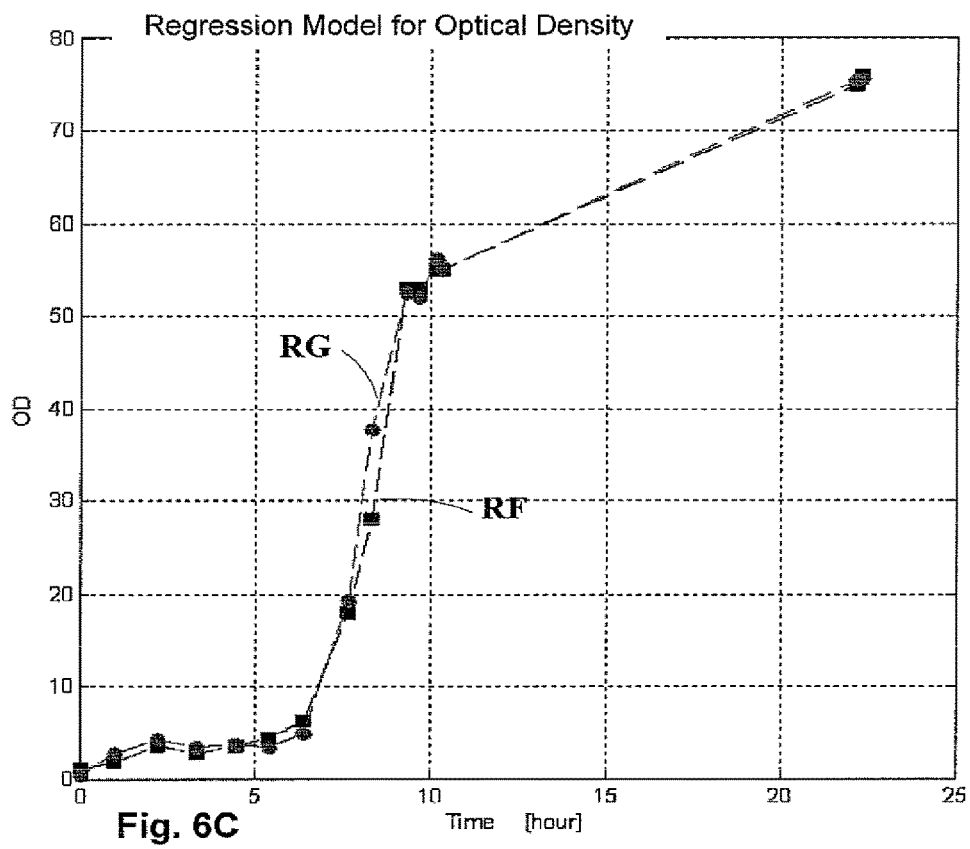

FIG. 6C is a graphical illustration showing two regression and reference plots, RG and RF, corresponding to the optical density of a biological material as a function of time. Plot RF is a reference plot obtained by direct measurements of the optical density taken during the experimental fermentation run. The regression plot RG is obtained during the experimental fermentation run by processing the measured $CO_2$ concentration based on the regression model which is used according to the present invention. As shown in the graphs the OD results obtained by the regression model based on the $CO_2$ concentrations are similar and almost same as those obtained by direct OD measurements.

The parameters of the regression model are estimated by means of the robust regression algorithm based on equations 11 and 12 as described above. More specifically, the robust regression operates by assigning a weight to each data point. Weighting is done automatically and iteratively using a process known as iteratively reweighted least squares. In the first iteration, each point is assigned equal weight and model coefficients ($\beta i$ in equation 11 above) are estimated using ordinary least squares. At subsequent iterations, weights are recomputed, so that points, which were farther from model predictions in the previous iteration, are given lower weight. The model coefficients are then recomputed using weighted least squares. The process continues until the values of the coefficient estimates converge within a specified tolerance.

The regression model used in this experiment utilizes the following regression coefficients $\beta i$ between response variable OD (y in equation 11 above) and the regressor/predictor variables ($x_i$ in equation 11 above) including: C, TV, RPM, pH and TEMP. To this end the following regression model was used for the estimated model parameters for prediction of OD from the measured values of $CO_2$ concentration and additional measured parameters of the fermentation process (the estimated OD being indicative of the biomass amount):

$$OD = 0.38 + 0.17 * TV + 2.06 * C + 0.0013 * (RPM - 50) + 22.07 * (pH - 7.0) - 0.95 * (TEMP - 37) \quad (13)$$

Figure 6D:
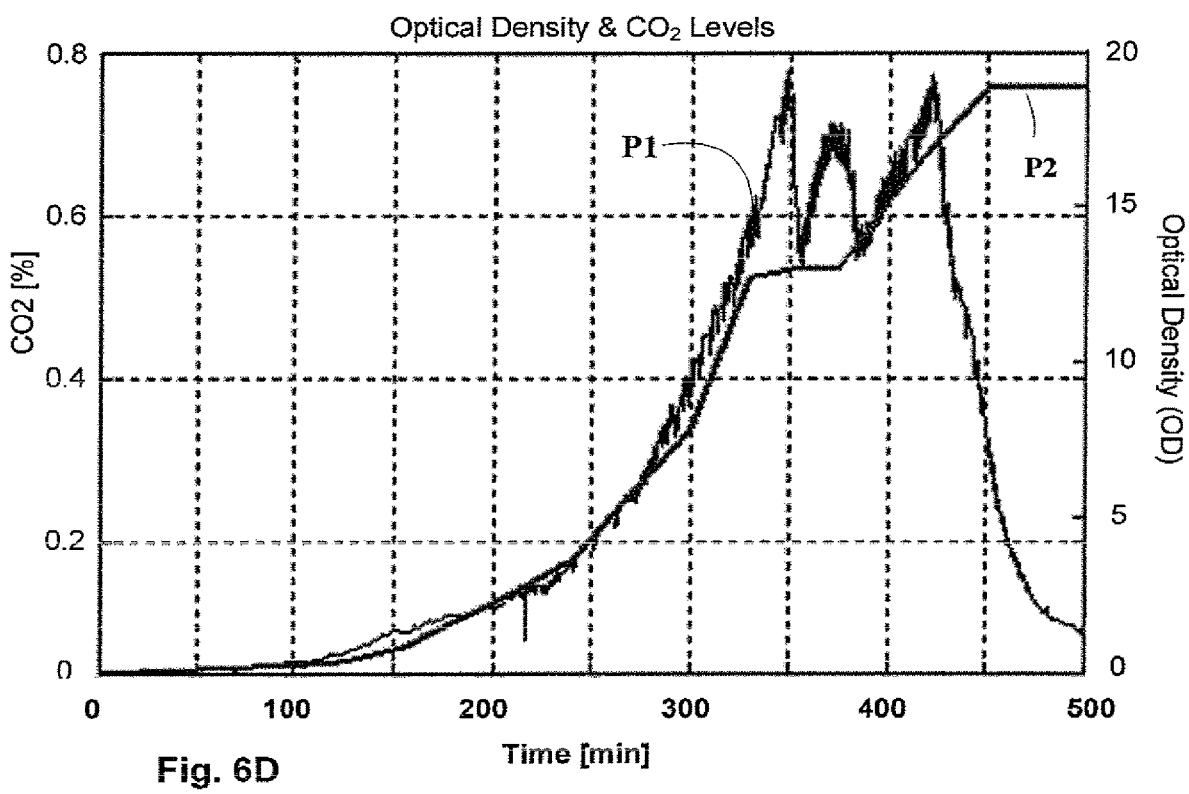

FIG. 6D shows the experimental results for a measured plot P1 of $CO_2$ concentration (left y axis) and the plot P2 of OD (right y axis) as a function of time. As shown in the figure there is a correlation between the OD and $CO_2$ measurements through during first 325 minutes of the experiment. Then, due to stress in carbon source, the bacteria/microorganisms keep growing with alternative metabolic cycles, as seen in $CO_2$ concentration plot P1. When the biomass/microorganisms die, the $CO_2$ decreases while the OD parameter stays constant.

Figure 7A:
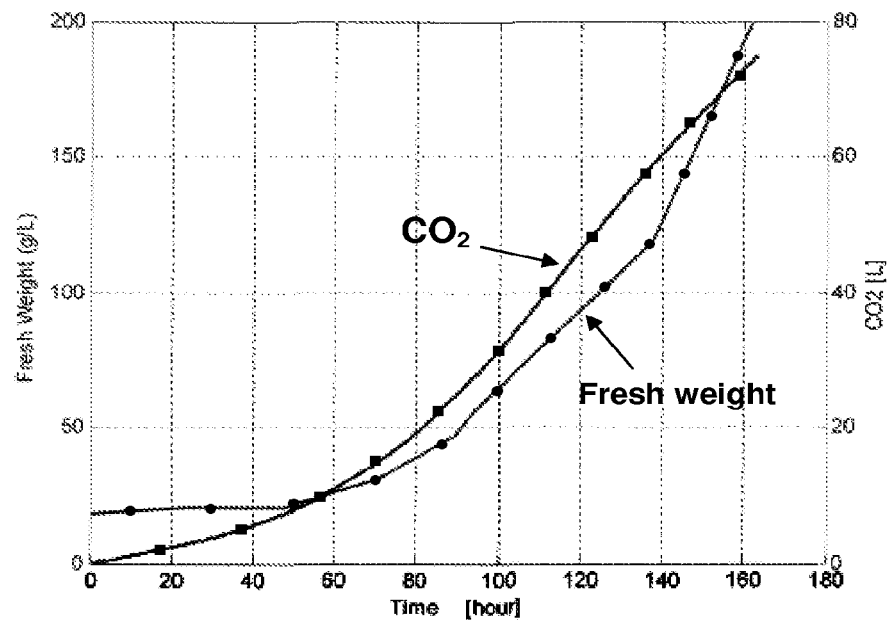
FIGS. 7A and 7B show experimental results for the monitoring of plant cells growth by $CO_2$ online measurements performed with the device and method of the present invention versus standard routine measurements of fresh weight (FIG. 7A) or conductivity (FIG. 7B)
Figure 7B:
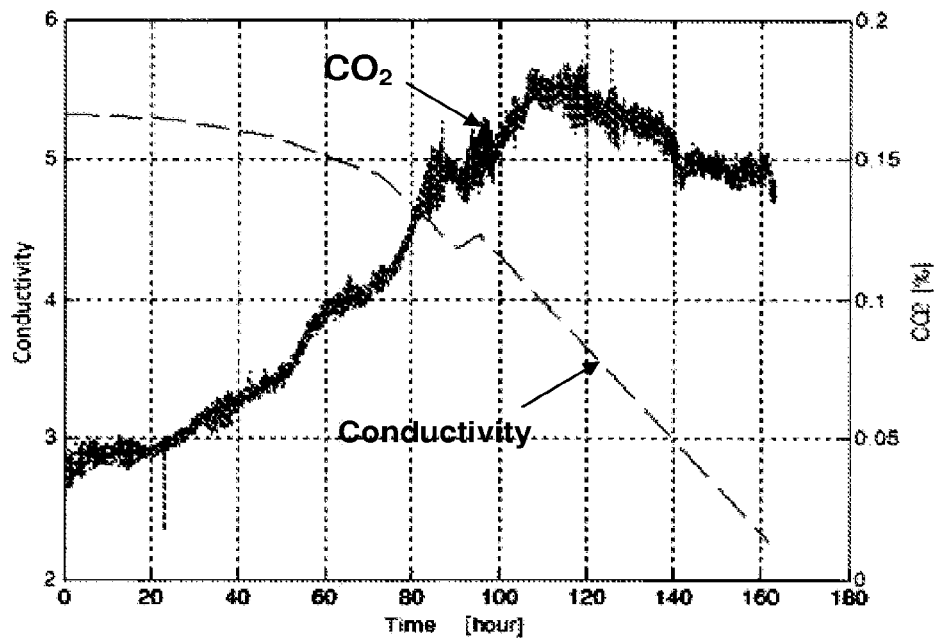

FIGS. 7A and 7B show plant cells growth monitoring by $CO_2$ online measurement made with the device and method of the invention versus fresh weight or conductivity measurements. The measurements have been conducted for plant cells in disposable fermenters. The high resolution of the device of the invention (1 ppm sensitivity) and continuous (real time) $CO_2$ measurements show a very high correlation with cell proliferation as measured by standard methodologies (fresh weight or conductivity). FIG. 7A shows the total volume of $CO_2$ gas emitted by plant cells vs time, during the whole experimental run correlates with fresh weight. Time=0 is the seeding time. The total $CO_2$ is correlated with the biomass and growth rate. This quantity was calculated using formula (14):

$$V(t) = \text{rate} \times \int_o^t s(t) dt \qquad (14)$$

where V(t) (in L) is the total volume of $CO_2$ gas emitted by the cells since the beginning of the run, rate is the aeration rate (in L/min), s(t) is the concentration of $CO_2$ (in volume fraction) measured in emission gases from the bioreactor. s(t) does not contain the initial concentration measured at the beginning of the run prior to the seeding time, which was subtracted from s(t), FIG. 7B shows the % concentration of $CO_2$ gas emitted by plant cells vs time, and correlation with conductivity, during the whole experimental run.

Figure 8:
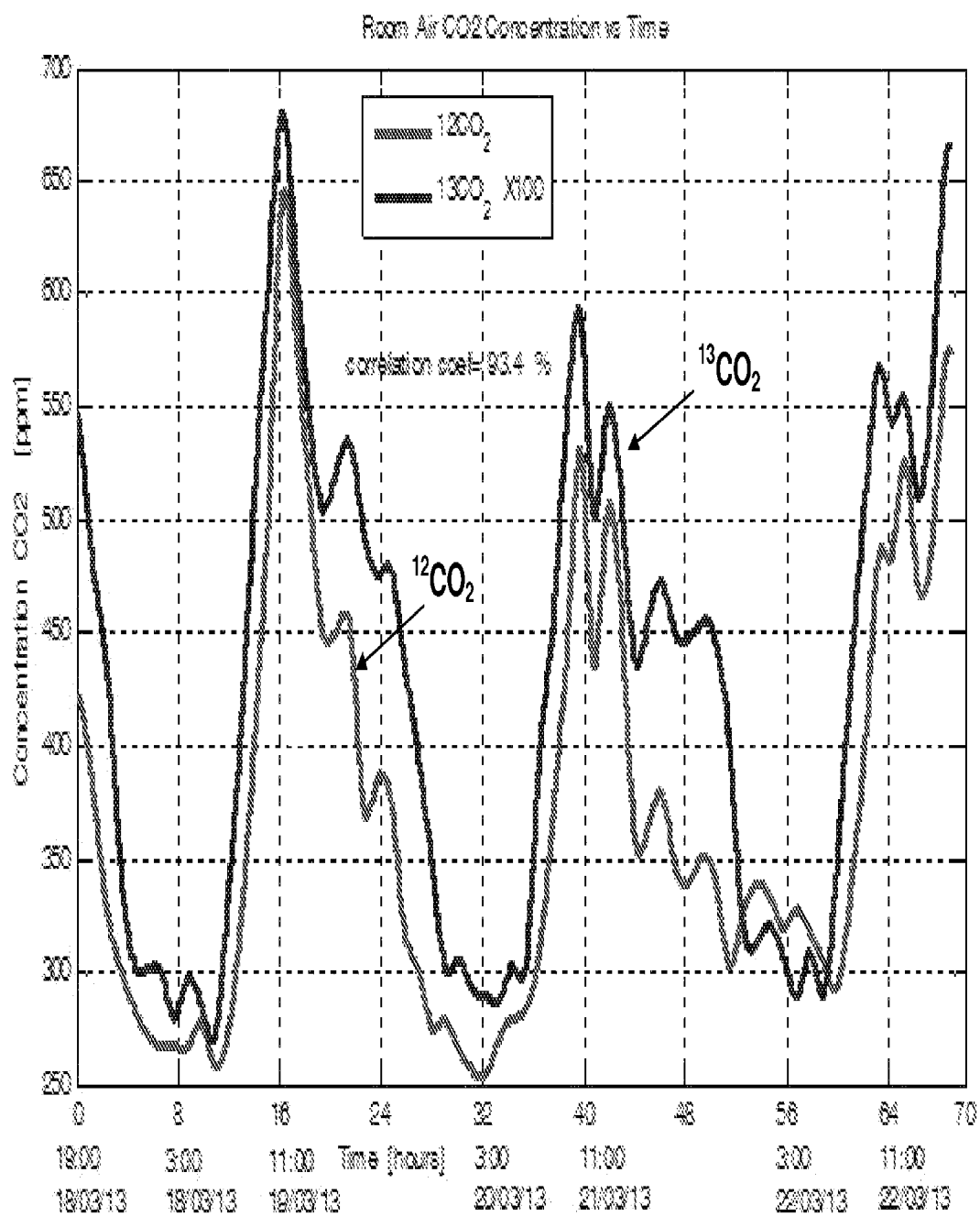
FIG. 8 shows experimental results regarding the detection of carbon dioxide ($^{12}CO_2$) and an isotopologue thereof ($^{13}CO_2$), vs time, with very high sensitivity (1 ppm order)

FIG. 8 shows experimental results demonstrating that the device and method of the invention can be employed for detecting isotopologues of a metabolic gas, such as carbon dioxide, with a very high sensitivity. In this experiment the presence of people in an office was monitored during five days based on the concentration of $^{12}CO_2$ and $^{13}CO_2$. The results show that late afternoon, when people were leaving, the total concentration of $CO_2$ was decreasing while, in the morning, the total concentration of $CO_2$ was increasing. It also shows that the device of the invention was able to detect variations of $^{12}CO_2$ concentration in the air between 0 and 0.07% (below 700 ppm), but also very slight variations of $^{13}CO_2$ concentration in the ppm order, namely between 0 and 7 ppm (about 1% of the total concentration of $CO_2$ is composed of isotopologue $^{13}CO_2$). For the sake of clarity, the curve showing the concentration of $^{13}CO_2$ has been represented with a x100 scale.

Figure 9:
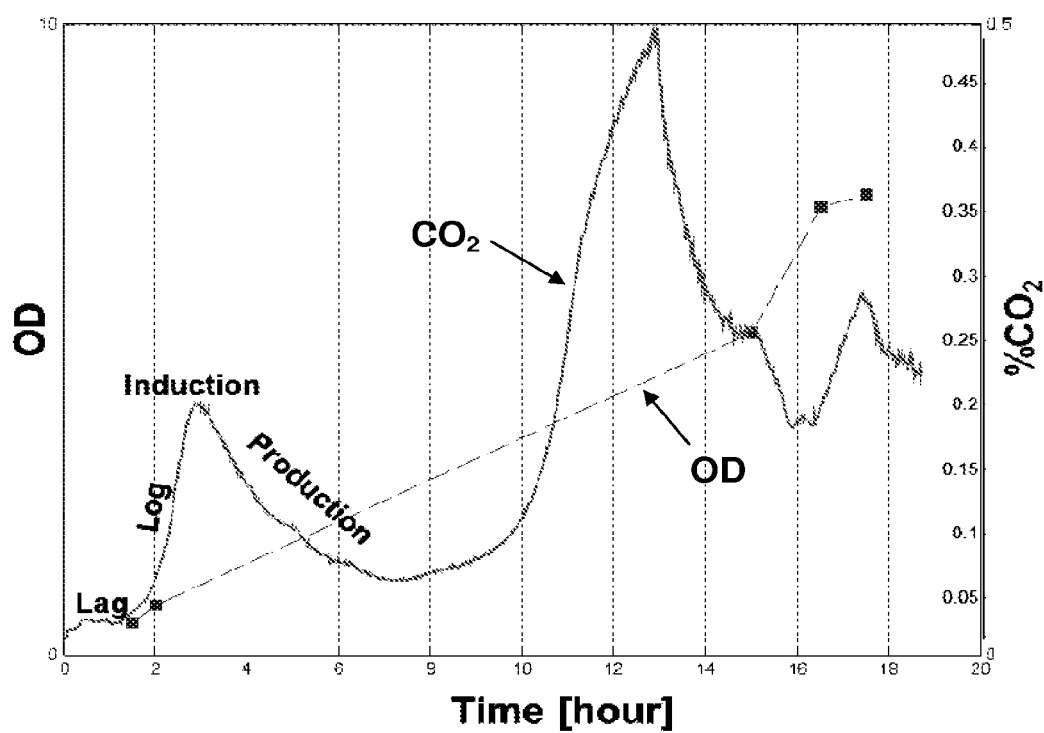
FIG. 9 shows experimental results comparing real-time and continuous monitoring of carbon dioxide performed according to the present invention versus manual sample measurements of biomass via optical density measurements (OD)

FIG. 9 shows experimental results demonstrating the advantages of the online and continuous monitoring of bacteria growth via detection of carbon dioxide concentration by the method and device of the invention (continuous line) versus periodic optical density manual measurements (dashed line). The lag phase (first 1.5 h) and log phase (1.5 h-3 h) can be clearly seen with the method of the invention but not with OD measurements. Furthermore, IPTG induction at h=3 and its blocking effect on bacterial replication can be clearly monitored (time during which the protein of interest is produced). Routine OD measurements were taken 4 times to monitor the fermentation process (at about h=1.75, 2, 16.25 and 17.75) while the method and device of the invention enable a continuous monitoring of the bacterial population. Thanks to the present method, it has been shown that bacterial replication restarted at h=10 and that a further IPTG induction would have been possible to optimize the production process.

Thus, the present invention provides novel, effective and simple techniques for accurate in-situ real time non-invasive monitoring of a biological material by monitoring metabolic gases in the dead space associated with the biological material. The biological material that can be monitored/inspected utilizing the invention includes but is not limited to sugars, proteins, or nucleic acids, or a combination of these substances. They may also be living entities, such as cells and tissues. They may be made from a variety of natural resources—human, animal, plant and other microorganism—and may be produced by biotechnology methods. Example of biological product is blood transfusion products such as RBC, platelets and plasma. The biological materials may include food product (food microbiology products). Bacterial viability determination is one of the major concerns in the food industry because injured bacteria cause a significant health threat if they revive during food distribution and storage and it is important to examine the efficacy of various intervention treatments used in food processing. Also, the invention provides for effective monitoring of a fermentation process, where micro-organisms are exploited to produce a wide variety of products such as dairy products (cheese, yogurt), beverages (beer, wine), single cell proteins (SCP), antibiotics, chemicals (citric and acetic acid, amino acids, enzymes, vitamins), fuels (ethanol, methanol, methane). Those skilled in the art will readily appreciate that various modifications and changes can be applied to the embodiments of the invention as hereinbefore exemplified without departing from the scope thereof defined in and by the appended claims.

The invention claimed is:

1. A method for in-situ real-time non-invasive estimation of a level of living cells proliferation and/or growth in a biological material present in a container sealed to prevent biological contamination, the method comprising measuring a concentration of at least one metabolic gas emitted by the living cells according to the following steps:
   (i) providing a container sealed to prevent biological contamination and enclosing a biological material;
   (ii) providing an optical system comprising:
      (a) a tunable coherent infrared light source adapted to emit (a) a first substantially monochromatic infrared light beam with wavelengths overlapping with an absorption peak of the metabolic gas; and (b) a second substantially monochromatic infrared light beam with wavelengths overlapping with a transmission peak of the metabolic gas or being outside an absorption spectrum of the metabolic gas;
      (b) a detection module configured for detecting the first and the second substantially monochromatic infrared light beams following their passage through a region of interest being part of the sealed container or in fluid communication with it, wherein the region of interest is free of the biological material; and further configured for generating data indicative of light intensity values corresponding to the first and the second substantially monochromatic infrared light beams transmitted through the region of interest; and
      (c) a control system connectable to the light source and the detection module the control system configured to operate the light source, to receive and analyze the data provided by the detection module, and to process the data provided by the detection module, to determine the concentration of the metabolic gas in the sealed container;
   (iii) determining the concentration of the metabolic gas emitted by the living cells, which is present in the region of interest, the region of interest being part of the container or in fluid communication with the container, wherein the region of interest does not contain the biological material, by:
      (a) positioning the region of interest between the tunable coherent infrared light source and the detection module of the optical system;

(b) applying the first substantially monochromatic infrared light beam with wavelengths overlapping with an absorption peak of the at least one metabolic gas and measuring the signal with said the detection module;

(c) applying a second substantially monochromatic infrared light beam with wavelengths overlapping with a transmission peak of the metabolic gas or being outside the absorption spectrum of the metabolic gas and measuring the signal with said the detection module;

(d) determining the concentration of the metabolic gas by processing the results obtained in (b) and (c); and (e) optionally repeating steps (b) to (d) at least one more time;

wherein the concentration c of the metabolic gas is determined in step (iii)(d) from n measured values of the signal $S_i$ (i=1, 2, . . . , n) at different wavelengths $\lambda_i$ by utilizing nonlinear minimization of a model $S(x, \lambda i)$ as provided by function s(x) below:

$$s(x) = \sum_{i=1}^{n-1} \left[ \log\left(\frac{S(x, \lambda_i) + \epsilon}{S(x, \lambda_n)}\right) - \log\left(\frac{S_i + \epsilon}{S_n}\right) \right]^2$$

where ε is a noise level at the detection module, and $S(x, \lambda_i)$ is provided by the following equation:

$$S(x,\lambda_i) = b \int_{\lambda_{min}}^{\lambda_{max}} f(\lambda - \lambda_i) e^{-\alpha_\lambda (x + c_0 l_0)} d\lambda$$

where b is a constant, $f(\lambda - \lambda_i)$ is the laser spectral distribution function around the central wavelength $\lambda_i$, $\alpha_\lambda$ is the absorption coefficient, x=cl wherein c is the gas concentration inside the container, l is the pathlength inside the container, $c_0$ is the concentration of the probed gas outside the container and $l_0$ is the pathlength outside the container between the infrared source and the detection module; and wherein the concentration of the metabolic gas is an indication of the level of living cells proliferation and/or growth in said the sealed container.

2. The method of claim 1, wherein the biological material present in the container sealed to prevent biological contamination is selected from a group consisting of blood components, cell cultures, and microorganisms in a fermentation process.

3. The method of claim 1, wherein a distance between the central wavelengths of the first substantially monochromatic infrared light beam and the second substantially monochromatic infrared light beam is less than the distance between two adjacent absorption peaks of the at least one metabolic gas.

4. The method of claim 1, wherein a spectral width of the first substantially monochromatic infrared light beam is wider than that of the absorption peak of the at least one metabolic gas but narrower than a distance between two adjacent absorption peaks of the metabolic gas.

5. The method of claim 1, wherein the concentration of the metabolic gas is measured with a sensitivity of 1-10 ppm and a dynamic range of 0-100% relative gas concentration.

6. The method of claim 1, wherein the metabolic gas is selected from the a group consisting of carbon dioxide, oxygen, ammonia, hydrogen sulfide, methane, ethane, butane, ethylene, sulfur dioxide, carbonyl sulfide and nitric oxide, and isotopologues thereof.

7. The method of claim 1, wherein the container sealed to prevent biological contamination is permeable to the at least one metabolic gas and wherein an emission rate of the metabolic gas is determined by applying the following formula:

$$W(t) = (\rho(t) - \rho^0) v A$$

where W(t) is the metabolic gas emission rate of enclosed biological material in units kg/s, ρ(t) is the mass concentration of the metabolic gas in units kg/m³ at time t, that is determined in step (iii)(d), $\rho^0$ is the ambient mass concentration of the gas, v is the membrane permeability coefficient to metabolic gas in units m/s, and A is the surface area of the membrane.

8. The method of claim 1, wherein the sealed container sealed to prevent biological contamination is not permeable to the metabolic gas and wherein the concentration of the metabolic gas is determined in step (iii)(d) by applying the following formula:

$$W(t) = (\rho(t) - \rho(t-\tau)) V / \tau$$

where W(t) is the metabolic gas emission rate of enclosed biological material averaged over time interval τ, and V is the volume of the container, and ρ(t) is the mass concentration of the metabolic gas at time t, that is determined in step (iii)(d).

9. A method for detecting a microorganism contamination in a storage container for platelets sealed to prevent biological contamination, the method comprising applying the method according to claim 6 for measuring the concentration of carbon dioxide emitted by the microorganism in the storage container that is sealed to biological contamination.

10. A method for monitoring a fermentation process in a fermentation container enclosing microorganisms and sealed to prevent biological contamination, the method comprising monitoring the amount of the microorganisms by applying the method according to claim 6 for measuring the concentration of carbon dioxide emitted by the microorganisms in the fermentation container that is sealed to prevent biological contamination.

11. A method for monitoring the concentration of living cells in a bioreactor sealed to prevent biological contamination, the method comprising applying a method according to claim 6 to measure the concentration of carbon dioxide emitted by the living cells in the bioreactor.

12. The method of claim 10 comprising correlating the concentration of carbon dioxide to an amount of biomass of the living cells via a linear or robust regression mathematical model, which is a pre-computed model calculated utilizing statistical regression analysis for modeling the relationship between one or more parameters such as predictor x, regressor variable(s), and one or more other parameters such as response variable(s) y;

wherein to estimate biomass the regressor/predictor variable(s), $(x_i)$ include the concentration C of $CO_2$ measured in the gases emitted from the fermentation container and/or Total Volume (TV) of $CO_2$ emitted from the beginning of fermentation, and the response variable (y) may include the optical density OD of the biological material in the container and l or the viable count VC, in this case the response variables (y) are related to k repressor's, $x_1, x_2, \ldots, x_k$ according to the following formula:

$$y = \beta_0 + \beta_1 x_1 + \beta_2 x_2 + \ldots \beta_k x_k + \epsilon.$$

* * * * *